United States Patent
Yanai et al.

(10) Patent No.: US 8,677,941 B2
(45) Date of Patent: Mar. 25, 2014

(54) SYSTEM AND METHODS FOR HEALTH MONITORING OF ANONYMOUS ANIMALS IN LIVESTOCK GROUPS

(75) Inventors: Ehud Yanai, Kiryat-Tivon (IL); Ron Elazari-Volcani, Moshav Ein-Sarid (IL)

(73) Assignee: Faunus Ltd., Tel-Aviv (IL)

( * ) Notice: Subject to any disclaimer, the term of this patent is extended or adjusted under 35 U.S.C. 154(b) by 0 days.

(21) Appl. No.: 13/613,087

(22) Filed: Sep. 13, 2012

(65) Prior Publication Data

US 2013/0006065 A1 Jan. 3, 2013

Related U.S. Application Data

(62) Division of application No. 12/320,719, filed on Feb. 3, 2009, now Pat. No. 8,297,231.

(51) Int. Cl.
*A01K 29/00* (2006.01)

(52) U.S. Cl.
USPC .......................................... 119/174

(58) Field of Classification Search
USPC .............. 119/14.14, 719, 720, 721, 851, 908, 119/174
See application file for complete search history.

(56) References Cited

U.S. PATENT DOCUMENTS

| | | |
|---|---|---|
| RE33,600 E | 6/1991 | Timmons |
| 5,474,085 A | 12/1995 | Hurnik et al. |
| 5,573,179 A | 11/1996 | Timmons et al. |
| 5,813,599 A | 9/1998 | Hoff |
| 5,956,463 A | 9/1999 | Patrick et al. |
| 5,983,837 A | 11/1999 | Briggs et al. |
| 6,287,264 B1 | 9/2001 | Hoffman |
| 6,308,660 B1 * | 10/2001 | Coiro et al. ................... 119/419 |
| 6,450,128 B1 | 9/2002 | Boyce |
| 6,782,845 B1 * | 8/2004 | Schmidt et al. ............... 119/419 |
| 7,026,939 B2 | 4/2006 | Letkomiller et al. |
| 7,180,424 B2 * | 2/2007 | Eyal ........................... 340/573.1 |
| 7,331,310 B1 | 2/2008 | Sersland et al. |
| 7,467,603 B2 | 12/2008 | Davies |
| 7,527,023 B2 | 5/2009 | Davies |
| 7,673,587 B2 | 3/2010 | Davies |
| 7,705,736 B1 | 4/2010 | Kedziora |
| 8,066,179 B2 | 11/2011 | Lowe |
| 8,297,231 B2 | 10/2012 | Yanai et al. |

(Continued)

FOREIGN PATENT DOCUMENTS

| | | |
|---|---|---|
| CN | 1464466 | 12/2003 |
| CN | 1963712 | 5/2007 |

(Continued)

OTHER PUBLICATIONS

English-language translation of JP2005-278547.*

(Continued)

*Primary Examiner* — Rob Swiatek
*Assistant Examiner* — Lisa Tsang

(57) ABSTRACT

A system and method for tracking the health of a group of livestock. In an exemplary embodiment of the invention, the vital signs of a small number of sentinel animals is tracked and used to assess the existence and/or progress of a disease in the group. In an exemplary embodiment of the invention, the vital signs are assessed using a vitality sensor, for example, an accelerometer which provides signals indicating the type and/or other properties of movements made by the sentinel animals.

20 Claims, 15 Drawing Sheets

(56) References Cited

U.S. PATENT DOCUMENTS

| | | |
|---|---|---|
| 2002/0010390 A1 | 1/2002 | Guice et al. |
| 2003/0004403 A1 | 1/2003 | Drinan et al. |
| 2003/0212348 A1 | 11/2003 | Lambert |
| 2005/0162279 A1 | 7/2005 | Marshall et al. |
| 2006/0150920 A1 | 7/2006 | Patton |
| 2007/0044732 A1 | 3/2007 | Araki et al. |
| 2007/0266959 A1 | 11/2007 | Brooks |
| 2007/0267358 A1 | 11/2007 | Stanford et al. |
| 2008/0203178 A1 | 8/2008 | Barrett et al. |
| 2010/0198023 A1 | 8/2010 | Yanai et al. |
| 2010/0198024 A1 | 8/2010 | Elazari-Volcani et al. |
| 2013/0125835 A1 | 5/2013 | Sinn et al. |

FOREIGN PATENT DOCUMENTS

| | | |
|---|---|---|
| CN | 101431596 | 5/2009 |
| CN | 101472469 | 7/2009 |
| CN | 101894220 | 11/2010 |
| CN | 202068839 | 12/2011 |
| CN | 202121610 | 1/2012 |
| CN | 102521400 | 6/2012 |
| DE | 19732957 | 11/1998 |
| EP | 0624313 | 11/1994 |
| EP | 0808567 | 11/1997 |
| EP | 0988786 | 3/2000 |
| EP | 1080638 | 3/2001 |
| EP | 1212939 | 6/2002 |
| EP | 1219170 | 7/2002 |
| GB | 2307054 | 5/1997 |
| JP | 05-268853 | 10/1993 |
| JP | 06-209670 | 8/1994 |
| JP | 11-225599 | 8/1999 |
| JP | 2001-275509 | 10/2001 |
| JP | 2002-354959 | 12/2002 |
| JP | 2005-058056 | 3/2005 |
| JP | 2005-278547 | 10/2005 |
| WO | WO 95/16343 | 6/1995 |
| WO | WO 96/09576 | 3/1996 |
| WO | WO 01/67853 | 9/2001 |
| WO | WO 02/13938 | 2/2002 |
| WO | WO 2005/048699 | 6/2005 |
| WO | WO 2005/082134 | 9/2005 |
| WO | WO 2008/001367 | 1/2008 |
| WO | WO 2008/072705 | 6/2008 |
| WO | WO 2010/071414 | 6/2010 |
| WO | WO 2010/089747 | 8/2010 |
| WO | WO 2010/089748 | 8/2010 |
| WO | WO 2011/120529 | 10/2011 |
| WO | WO 2012/154841 | 11/2012 |

OTHER PUBLICATIONS

English-language translation of CN 101472469.*
International Preliminary Report on Patentability Dated Aug. 18, 2011 From the International Bureau of WIPO Re. Application No. PCT/IL2010/000105.
International Preliminary Report on Patentability Dated Aug. 18, 2011 From the International Bureau of WIPO Re. Application No. PCT/IL2010/000107.
International Search Report and the Written Opinion Dated Aug. 3, 2010 From the International Searching Authority Re. Application No. PCT/IL2010/000105.
International Search Report Dated Jun. 18, 2010 From the International Searching Authority Re. Application No. PCT/IL2010/000107.
Notice of Allowance Dated Jul. 6, 2012 From the US Patent and Trademark Office Re. U.S. Appl. No. 12/320,719.
Official Action Dated Sep. 2, 2011 From the US Patent and Trademark Office Re. U.S. Appl. No. 12/320,719.
Official Action Dated Jul. 14, 2011 From the US Patent and Trademark Office Re. U.S. Appl. No. 12/320,719.
Official Action Dated Feb. 15, 2012 From the US Patent and Trademark Office Re. U.S. Appl. No. 12/320,720.
Official Action Dated Jan. 24, 2012 From the US Patent and Trademark Office Re. U.S. Appl. No. 12/320,719.
Official Action Dated Aug. 28, 2012 From the US Patent and Trademark Office Re. U.S. Appl. No. 12/320,720.
Response Dated Aug. 14, 2011 to Official Action of Jul. 14, 2011 From the US Patent and Trademark Office Re. U.S. Appl. No. 12/320,719.
Cobb "Broiler Management Guide", Cobb-Vantress.com, p. 1-65, Dec. 1, 2010.
EPO "Notice From the European Patent Office Dated Oct. 1, 2007 Concerning Business Methods / Mitteilung des Europaeischen Patentamts vom Oct. 1, 2007 ueber Geschaeftsmethoden / Communique de l'Office Europeen des Brevets, en Date du 1er Oct. 2007, Concernant les Methodes dans le Domaine des Activites", Amtsblatt des Europaeischen Patentamts / Official Journal of the European Patent Office / Journal Officiel de l'Office Europeen des Brevets, XP002498048, 30(11): 592-593, Nov. 1, 2007. Basis for the Declaration That Documentary Evidence Is Not Required Due to the Notoriety of the Claimed and Disclosed Subject-Matter, p. 593, § 2.
EPO"Notice From the European Patent Office Dated Oct. 1, 2007 Concerning Business Methods / Mitteilung des Europaeischen Patentamts vom Oct. 1, 2007 ueber Geschaeftsmethoden / Communique de l'Office Europeen des Brevets, en Date du 1er Oct. 2007, Concernant les Methodes dans le Domaine des Activites", Amtsblatt des Europaeischen Patentamts / Official Journal of the European Patent Office / Journal Officiel de l'Office Europeen des Brevets, XP002498048, 30(11): 592-593, Nov. 1, 2007. Basis for the Declaration That Documentary Evidence Is Not Required Due to the Notoriety of the Claimed and Disclosed Subject-Matter, p. 593, § 2.
EPO "Statement in Accordance With the Notice From the European Patent Office Dated Oct. 1, 2007 Concerning Business Methods—PCT / Erklaerung Gemaess der Mitteilung des Europaeischen Patentamts vom Oct. 1, 2007 ueber Geschaeftsmethoden—PCT / Declaration Conformment au Communique de l'Office Europeen des Brevets en Date du 1er Oct. 1, 2007 Concernant les Methodes dans le Domaine des Activites Economiques - PCT", Amtsblatt des Europaeischen Patentamts / Official Journal of the European Patent Office / Journal Officiel de l'Office Europeen des Brevets, XP002498048, 30(11): 592-593, Nov. 1, 2007. The Technical Aspects Identified in the Present Application (Art. 15 PCT) Are Considered Part of Common General Knowledge. Due to Their Notoriety No Documentary Evidence Is Found to Be Required. For Further Details See the Accompanying Opinion.
EPO "Statement in Accordance With the Notice From the European Patent Office Dated Oct. 1, 2007 Concerning Business Methods—PCT / Erklaerung Gemaess der Mitteilung des Europaeischen Patentamts vom Oct. 1, 2007 ueber Geschaeftsmethoden—PCT / Declaration Conformment au Communique de l'Office Europeen des Brevets en Date du 1er Oct. 2007 Concernant les Methodes dans le Domaine des Activites Economiques—PCT", Amtsblatt des Europaeischen Patentamts / Official Journal of the European Patent Office / Journal Officiel de l'Office Europeen des Brevets, XP002498048, 30(11): 592-593, Nov. 1, 2007. The Technical Aspects Identified in the Present Application (Art. 15 PCT) Are Considered Part of Common General Knowledge. Due to Their Notoriety No Documentary Evidence Is Found to Be Required. For Further Details See the Accompanying Opinion.
Fukuda et al. "An Optimum Design Method Utilizing a Strategic System Design Concept—Reduction of CO2 Emissions at a Datacenter by Reusing Emitted Heat for Agiculture", Synthesiology, English Edition, 3(3): 189-196, Dec. 2010.
Itoh et al. "Development of a Sensor System for Animal Watching to Keep Human Health and Food Safety—A Health Monitoring System for Chickens by Using Wireless Sensors", Synthesiology, English Edition, 3(3): 224-233, Dec. 2010.
Katoh et al. "A Methology for Improving Reliability of Complex Systems—Synthesis of Architectural Design Method and Model Checking", Synthesiology, English Edition, 3(3): 197-213, Dec. 2010.
Nakamura et al. "National Electrical Standards Supporting International Competition of Japanese Manufacturing Industries—Realization of a New Capacitance Standard and Its Traceability System", Synthesiology, English Edition, 3(3): 214-223, Dec. 2010.

(56) References Cited

OTHER PUBLICATIONS

Suzuki et al. "Interview: Meta-Engineering That Promotes Innovation", Synthesiology, English Edition, 3(3): 234-239, Dec. 2010.
Communication Pursuant to Article 94(3) EPC Dated Sep. 21, 2012 From the European Patent Office Re. Application No. 10712166.7.
Supplemental Notice of Allowability and Examiner-Initiated Interview Summary Dated Oct. 5, 2012 From the US Patent and Trademark Office Re. U.S. Appl. No. 12/320,719.
Communication Pursuant to Article 94(3) EPC Dated Sep. 19, 2012 From the European Patent Office Re. Application No. 10712165.9.
5m Publishing "Challenges Facing the Global Poultry Industry to 2020", The Poultry Site, 5m Publishing, 6 P., 2000.
Dawkins et al. "Optical Flow, Flock Behaviour and Chicken Welfare", Animal Behaviour, 84(1): 219-223, Jul. 2012.
Figueiredo et al. "Development of Machine Vision Based Poultry Behavior Analysis System", Written for Presentation at the 2003 ASAE Annual International Meeting, Vegas, Nevada, USA Jul. 27-30, 2003, Paper No. 033083, p. 1-17, Jul. 2003.
Green et al. "The Place of Models in the New Technologies of Production Systems", Mechanistic Modelling in Pig and Poultry Production, Chap.15: 305-324, 2006.
Jorge de Moura et al. "Strategies and Facilities in Order to Improve Animal Welfare", Revista Brasileira de Zootecnia, 39: 311-316, 2010.
Penz Jr. et al. "Challenges Facing the Global Poultry Industry Until 2020", 22nd Annual Australian Poultry Science Symposium, Sidney, New South Wales, Australia, Feb. 14-16, 2011, 22: 49-55, 2011.
Penz Jr. et al. "The Future of Broiler Production in the Americas", Proceedings of Conferencia Facta de Ciencia e Technologia Avicola, 27: 1-9, 2009.
Office Action Dated Mar. 18, 2013 From the Federal Service of Intellectual Property, Federal State Budget Institute, Federal institute of Industrial Property of the Russian Federation Re. Application No. 2011136154 and Its Summary in English.
Translation of Examination Report Dated Mar. 13, 2013 From the Instituto Mexicano de la Propiedad Industrial Re. Application No. MX.a.2011/008206.
Burt "GrowSafe Technology Offers Potential to Monitor Feed Efficiency, Animal Behavior and Illness", ANGUS Journal, p. 164-167, Nov. 2004.
Examination Report Dated Apr. 18, 2013 From the Instituto Mexicano de la Propiedad Industrial Re. Application No. MX/a/2011/008205 and Its Summary in English.
Notification Dated Oct. 7, 2013 From the Federal Service of Intellectual Property, Federal State Budget Institute, Federal Institute of Industrial Property of the Russian Federation Re. Application No. 2011136154 and Its Summary in English.
Notification of Office Action Dated Aug. 16, 2013 From the State Intellectual Property Office of the People's Republic of China Re. Application No. 201080014426.2 and its Translation Into English.
Search Report Dated Aug. 16, 2013 From the State Intellectual Property Office of the People's Republic of China Re. Application No. 201080014426.2 and its Translation Into English.
Supplemental Notice of Allowability Dated Jan. 10, 2014 From the US Patent and Trademark Office Re. U.S. Appl. No. 13/613,087.

\* cited by examiner

SYSTEM AND METHODS FOR HEALTH MONITORING OF ANONYMOUS ANIMALS IN LIVESTOCK GROUPS

RELATED APPLICATION

This application is a division of U.S. patent application Ser. No. 12/320,719 filed on Feb. 3, 2009, now U.S. Pat. No. 8,297,231, the contents of which are incorporated herein by reference in their entirety.

FIELD AND BACKGROUND OF THE INVENTION

Farm livestock is exposed to disease as all living creatures are. The economical pressure of disease in farm livestock however, is enormously high.

Livestock diseases are usually detected (and defined) by personal inspection by the farmer or by the veterinarian—once a vast majority of the group is infected. A group may refer to a poultry flock, a group of hives gathered in one location, a herd of grazing sheep or cattle, a fishpond etc. This is the case for livestock groups containing a large number of individuals, in which the individual is "anonymous"—such as poultry, bees, grazing cattle or sheep, fish and others.

Because of the anonymity of the group members, health condition of individuals is not monitored—only that of the group—and diseases are detected too late. To minimize risk and losses, farmers usually rely on prophylactic treatments and massive usage of medications. This pattern of health control results in late detection of disease outbreak—sometimes by days or even weeks—leading to higher morbidity and mortality rates, consequently to higher damages and costs.

Poultry farming is industrialized in most countries. House temperature and humidity are automatically controlled. Feeding, watering and even vaccination and medication are delivered automatically.

Human presence inside the chicken house is deliberately kept at minimum and human inspection of the flock's productivity and health are remote and scarce.

These inspections are carried out once a day or two by the farmer or his employees and once a week or two by the veterinarian. Inspections are visual. Due to the large number of chickens in the flock (up to 200,000 per house of broilers), morbidity is usually only noticed once a large portion of the flock shows significant symptoms of a certain disease, or once mortality rate is high enough to be noticed. By that time, up to 100% of the flock could be infected, treatment required is massive and the economical losses caused by reduction of production and mortality are heavy.

As of today, this is the common and standard procedure in the industry for health monitoring and disease outbreak detection in commercial flocks of poultry.

In many poultry diseases, such as Coccidiosis, respiratory diseases and others, a vast damage is inflicted on the farmer and that damage increases daily until the disease is detected, identified and properly treated. Late detection of the disease might lead (in severe cases) even to a total destruction of the entire group. The well known "Avian flue" (or bird's flu) is a good example of the vast damage inflicted on farmers once the disease is detected in a flock. Not only will the infected flock be destroyed, but other flocks in a radius of 3 km. as well. Direct damages of such single occurrence could accumulate to millions of dollars.

There are about 1.5 million commercial poultry houses (broilers, layers, turkeys, hatcheries and others) around the globe. Health costs of these flocks mounts to 10% of all production costs (costs of productivity reduction, consequential to morbidity are excluded), while mortality percentage in these flocks averages 4%-8%.

There is a need for new health monitoring concept and technology that will dramatically reduce these cost factors and may eventually bring about changes in veterinary regulations.

Similar limitations exist in other industries of livestock groups mentioned above.

SUMMARY OF THE INVENTION

According to a first aspect of the present invention there is provided a livestock groups computerized health monitoring system comprising: a storage and computing unit storing at least one database; a plurality of data collecting units of different types, each type comprising at least one sensor, said data collecting unit types selected from the group consisting of acoustic sensors, vitality meters, ammonia sensors, visual sensors and scent sensors; and first communication means for communicating operating commands from the storage and computing unit to each of the data collecting units and for communicating data from the data collecting units to the storage and computing unit.

The system may additionally comprise second communication means for communicating between the storage and computing unit and a user device.

The sensors may comprise identification means and wherein said first communication means comprise means for communicating operating command to a selected number of identified sensors.

The at least one database may comprise, for each parameter measured by the sensors, quantified records of the measured parameter and quantified records indicating normal status, abnormalities and pathologies.

The storage and computing unit may comprise software means for: computing said quantified records of the measured parameters; comparing the computed records to said quantified records indicating normal status, abnormalities and pathologies; and analyzing the comparison results.

The storage and computing unit may additionally comprise software means for analyzing said quantified records of the measured parameters for changes over time.

The system may additionally comprise alert means configured to communicate an alert to said user device upon detection of deviation from normal in data communicated by at least one of said data collecting unit types.

The user device may be selected from the group consisting of personal computer, telephone and mobile phone.

The system may additionally comprise means for acquiring data from external measuring systems selected from the group consisting of feeding, watering, weighting, temperature and humidity.

The acoustic sensors may comprise microphones and wherein said database comprises vocal signatures.

The vocal signatures may pertain to at least one of different parts of the day, different seasons, different stages of the group's development, different species and different breeds.

The visual sensors may comprise digital cameras capable of capturing the entire group, a specific zone or an individual.

The vitality meters are attached to a sample of statistically sufficient number of sentinels within the group.

Each sentinel may comprise at least one of an identification means and location means.

The livestock may comprise one of poultry, bees, cattle, sheep and goats.

According to a second aspect of the present invention there is provided a computerized method for monitoring the health of livestock groups, comprising the steps of: collecting measurements data from a plurality of data collecting units of different types, each type comprising at least one sensor, said data collecting unit types selected from the group consisting of acoustic sensors, vitality meters, ammonia sensors, visual sensors and scent sensors; computing quantified records of the measured parameters; comparing the computed records to pre-stored quantified records indicating normal status, abnormalities and pathologies; and analyzing the comparison results. The sensors may comprise identification means and said measurement data may be collected from a selected number of identified sensors.

The method may additionally comprise the step of categorizing said quantified records of the measured parameters in view of said comparison results as new normal, abnormal or pathological phenomena, according to predefined criteria.

The predefined criteria may comprise changes over time.

The method may additionally comprise the step of analyzing said quantified records of the measured parameters for changes over time.

The step of analyzing may comprise analyzing the comparison results of a plurality of measured parameters.

The method may additionally comprise the step of communicating an alert to a user device upon detection of deviation from normal in data communicated by at least one of said data collecting unit types.

The user device may be selected from the group consisting of personal computer, telephone and mobile phone.

The method may additionally comprise the step of acquiring data from external measuring systems.

The external measuring systems are selected from the group consisting of feeding, watering, weighting, temperature and humidity.

The pre-stored quantified records pertaining to the acoustic sensors comprise vocal signatures.

The stored vocal signatures may pertain to at least one of different parts of the day, different seasons and different stages of the group's development, different species and different breeds.

The method may additionally comprise the step of attaching said vitality meters to a sample of statistically sufficient number of sentinels within the group.

Each sentinel may comprise at least one of marking means and location means.

The livestock may comprise one of poultry, bees, cattle, sheep and goats.

BRIEF DESCRIPTION OF THE DRAWINGS

For a better understanding of the invention and to show how the same may be carried into effect, reference will now be made, purely by way of example, to the accompanying drawings.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DESCRIPTION OF SPECIFIC EMBODIMENTS OF THE INVENTION

Figure 1:
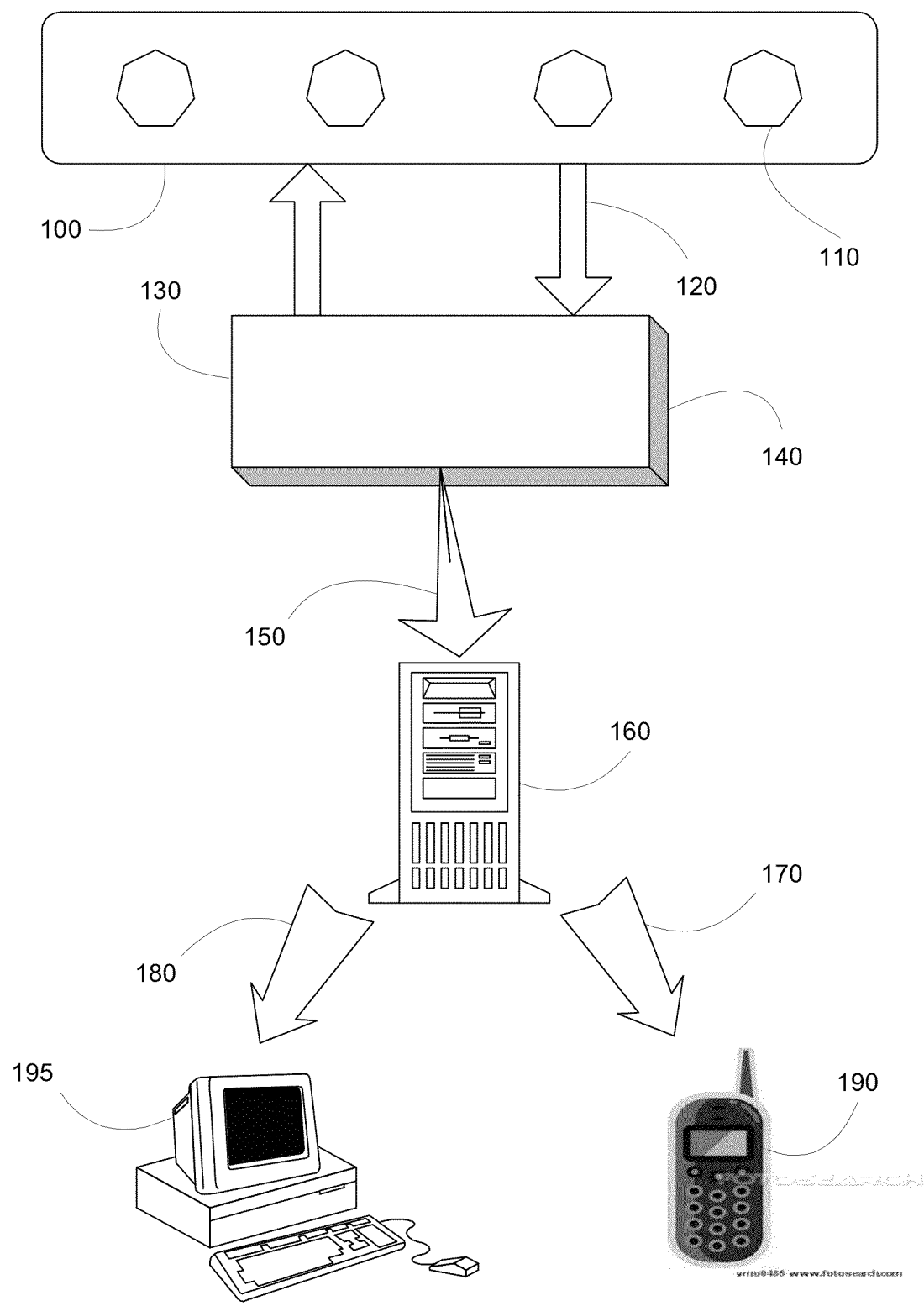
FIG. 1 is a schematic representation showing the various components of an exemplary system according to the present invention.

The "HEMOSYS" (Health monitoring system) is a data collector and a monitor of livestock's health status and disease outbreak—which revolutionizes the health control practices in poultry and other anonymous livestock groups.

This system presents, for the first time, a combined approach to livestock groups' health and its monitoring; a systemic quantified and automated approach of monitoring health parameters of the entire group on one hand, and individual approach, of monitoring a statistically sufficient number of individuals in the group on the other hand. Integration, processing and analysis of the data collected enables early and reliable detection of morbidity and disease outbreak.

This system is designed to enable real-time or near real-time monitoring of poultry and other livestock groups, by significant health parameters and behavioral patterns. The data is collected on site, saved and analyzed on the system server. Health status reports, analysis results and alerts are transmitted to the farmer/veterinarian by means of LAN hardware, internet, or by cellular phone which is integrated into the system.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated exemplary embodiments of the invention.

Other objects of the present invention will be evident to those of ordinary skill, particularly upon consideration of the following detailed description of exemplary embodiments.

FIG. 1 is a schematic representation showing the various components of an exemplary system according to the present invention.

The system comprises three main units:
1. Data collecting unit (100). A set of sensors and devices (110) for collecting essential data and transmitting (120) the collected data to the core (computing) unit (160).
2. Communication platform (140). This basic platform serves as bi-directional communication and control center. It operates and controls (130) its "Extension fingers"—the data collectors (110), receives data from the "fingers" and transmits the information (150) to the computing unit (160).
3. Computing unit (160) which includes data bases and analysis programs, integrated to the user hardware. This core computing unit utilizes smart algorithms constantly and continuously analyzing the flock's health status, compares the current status to healthy flock parameters, alerts for abnormalities and presents (170, 180) the flock's status to the end user interface (190, 195), be it a mobile phone, a laptop or any kind of computer system.

Data collecting unit (100) is an array of sensors and devices (110), sensing and transmitting predetermined data by means of low power local RF transmitter, by LAN or any other existing communications technology. Vital information on site indicating wellness status, activity and production rate parameters is gathered and submitted constantly on predetermined schedule.

The array (100) may include all, or part of the following means:
Video digital cameras—collecting visual information.
Such as: Sentry Model PT23DN-OD-OT, or PT23DN/ID, PTZ ¼' Color SONY Super HAD CCD DSP camera or similar.
http://wwwdotcctvsentrydotcom/
Acoustic sensors—collecting vocal information.
Such as: AKU2000 of wwwdotakusticadotcom, or Roga MI-17 with RogaDAQ2 (analyzer) of wwwdotroga-messtechnikdotde or similar.
Ammonia level detectors.
Such as: GCS512A AMMONIA DETECTOR of Storage Control Systems Inc., http://wwwdotstoragecontroldotcom/ammoniadotshtml, or GS-100/C gas sensor system by Greer Systems Automation, http://greersystemsdotcom/
Vitality meter units attached to a sample of statistically sufficient number of individuals (sentinels) in the group, for monitoring activity and other parameters;
Scent sensing devices (E-nose sniffers)—Such as: Griffin cheMSense 600, or Fido onboard by ICX Technologies, http://wwwdoticxtdotcom/
In house existing measuring systems: Weight, food and water consumption, humidity, house temperature etc.
Other detectors.

The communication platform (140) is a fully developed and operating unit for monitoring and control of remotely located electronic systems.

The unit delivers bi-directional information through LAN, RF, internet, cellular networks or any other communications technology and is accessible by mobile phones and computers at any location, at all times, such as: Bacsoft control system, http://wwwdotbacsoftdotcom/bacsoft_eng/index-dothtm.

The system server (160) stores and analyzes collected data using dedicated software. Smart algorithms analyze all data received from both the system's sensors and from on-site existing information mechanisms of weight gain, food and water consumption etc.

Pre-determination of standard scale of behavior, wellness, activity, and production rate is programmed into the system according to typical characteristics of these parameters for each species and sub-species, in each region and climate area, at each time of the year and development stage of the group.

Alert mode is operated upon occurrence of abnormal phenomena or extreme changes in critical parameters.

Communication management, protocols and controls are managed by the server.

The operational part of the server software activates data transfer from the sensing sub-systems on predetermined time intervals. This activation may be sequential or simultaneous. Some subsystems will collect data constantly, and transmit the collected data upon the above mentioned activation; others will collect and transmit data directly upon activation. Proper switching to each sub-system is made at the communication center. Activation may also be triggered for specific purposes by either (a) Manual command of the user or (b) Special command of the system whenever additional data is required for phenomenon analysis of the entire flock, specific group or zone or specific individuals.

Data collected from each sub-system is processed and analyzed by dedicated software (for each sub-system).

The data base on the server includes records of normal patterns for each parameter measured by the sub-systems. Once data is transmitted by any sub-system, the server will process and analyze this data specifically for that sub-system, as later described in the sub-systems description.

Results from all sub-systems are then being cross referenced and further analyzed with respect to the following contexts:
1. The group of sentinels. Changes within the group, relative position of each sentinel in the group and statistical change of patterns of the entire group, location and concentration of sentinels for which change has been detected.
2. Change of parameters in more than one sub-system. Statistical weight of each parameter and adjusted calculation of change significance. Comparison of results to predefined allowed limits of average, median, standard deviation and other tests.
3. Rate of changes. The program will analyze each change (and combined changes) in itself to define its rate. This datum is a significant criteria for triggering an alert— even with new (to the system) symptoms or otherwise insufficient data for decision making.

4. Zone analysis.
5. Specific special statistics.
6. Disease comparison and analytics. Some symptoms (or combination of symptoms) are indicative of certain diseases. These are programmed in the data base and the algorithm will compare the results to this file, in order to indicate the suspected disease and the probability of its occurrence.

Alerts may be activated by either: (a) Independent triggers of each sub-system's software and/or (b) Triggering results by criteria of the combined system analysis.

Result tables and charts—for each sub-system and for the entire system are constantly updated and may be displayed automatically or upon demand on the user interface.

Figure 2A:
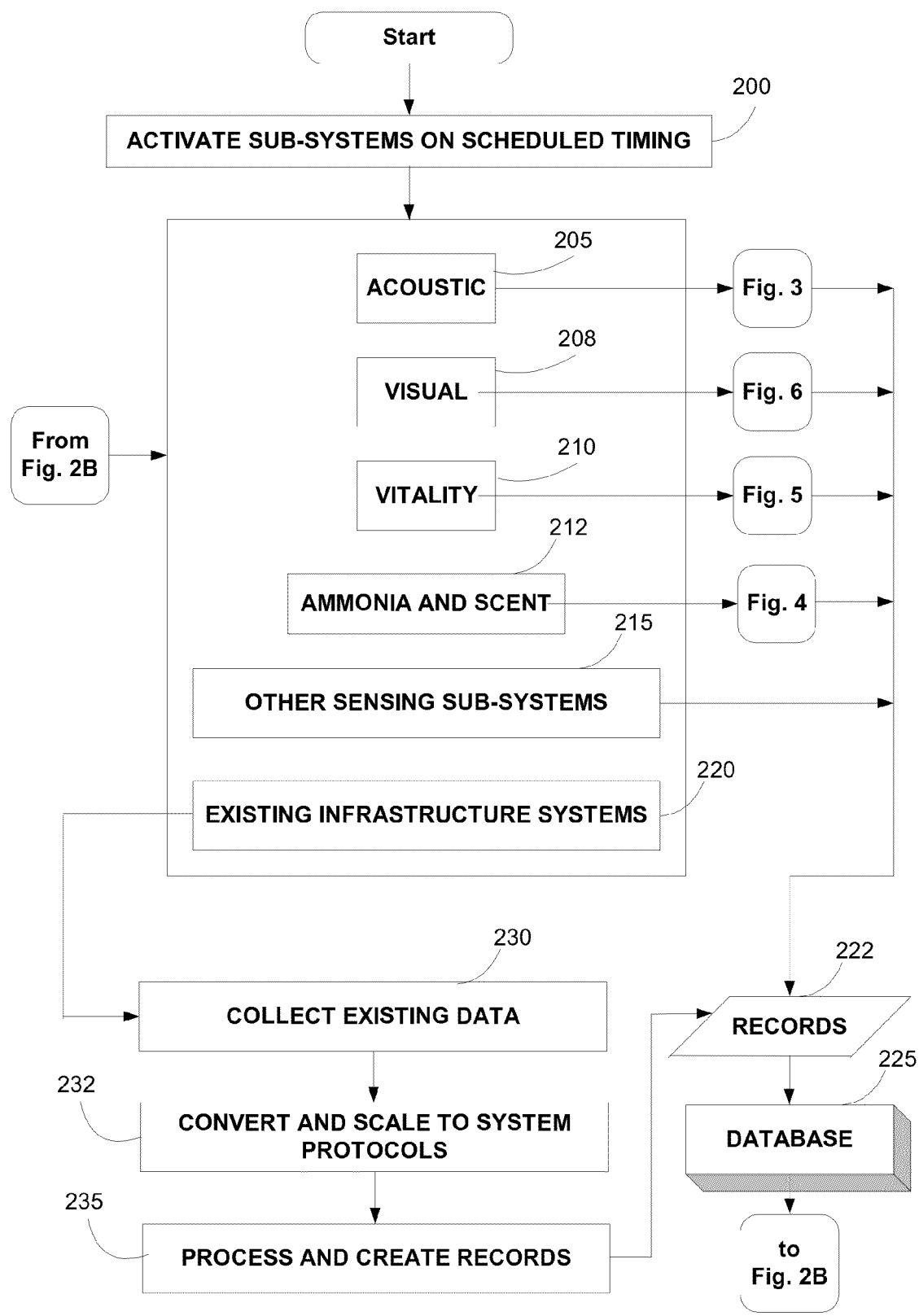
FIGS. 2A and 2B are an exemplary flowchart showing the operation of the system.
Figure 2B:
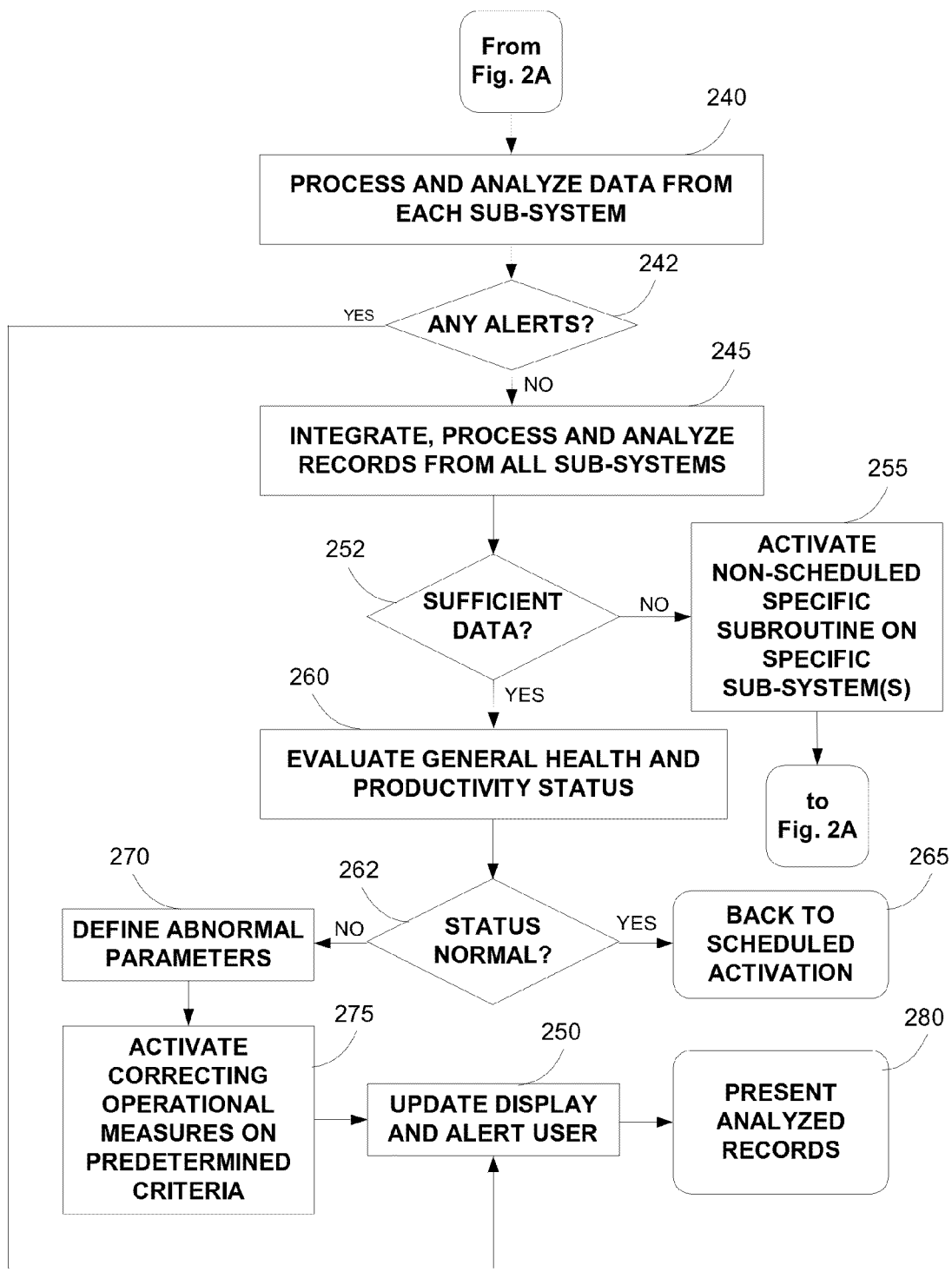

FIGS. 2A and 2B are an exemplary flowchart showing the operation of the system.

In step (200) the various sensing sub-system are operated on schedule. The sub-systems may comprise all or some of acoustic (205), visual (208), vitality (210), ammonia and scent (212), other various sensing sub-systems (215) and existing infrastructure systems (220) such as feeding, watering, weighting, humidity, temperature, etc. FIGS. 3, 4, 5 and 6 shows in detail the analysis performed in the acoustic, ammonia and scent, vitality and visual sub-systems, respectively. The data records (222) collected from these sub-systems and from other optional sensing sub-systems (215) are stored in the in the computer unit's (160) database (225). Data from existing infrastructure systems (220) is collected (230), converted and scaled to suit system protocols (232), formatted (235) into system records (222) and stored in the in the computer unit's (160) database (225).

In the system server, data from each sub-system is processed and analyzed (240, FIG. 2B). The analysis results are checked for alert conditions (242). If an alert condition exists, the system proceeds to display the alert on the user's display device (250) and presents the analyzed records to the user (280).

If no alert condition has been identified by analyzing each sub-system's data separately, the system proceeds to integrate process and analyze the combined records from all sub-systems (245). The combined data is checked for sufficiency (252). If the system determines that insufficient data exists for proper evaluation, the missing data is defined and the proper sub-system(s) are activated (255) out of the regular schedule. If the data is deemed to be sufficient, the system proceeds to evaluate the general health and productivity status of the flock (260), by comparison with pre-defined normal conditions (262).

If the status is determined to be within the normal range, the system cycles back to step (200, FIG. A) to resume scheduled actuation of the sensing sub-systems. Otherwise, the abnormal parameters are defined (270). The system then activates correcting operational measures (such as: Blowers, heaters, or alike) and proceeds to step (250) to alert the user and present the analyzed records (280).

Acoustic Sub-System

The acoustic sub-system according to the present invention comprises microphones scattered along the site. Scattering points are chosen and marked on a 3D map of the site, prepared prior to the system's positioning. These microphones are either (a) Wired to the communication center or (b) Include RF transceiver. The microphones are activated separately, by zone groups or all at once. Sounds collected are transmitted to the server, microphone number and time of collection defined and added to each record. Raw sound records are digitized and spectrum modulated, then processed and analyzed as shown in FIG. 3. Process includes (but is not limited to) quantification and manipulation of digitized data (frequency and amplitude) along a time scale, analysis of changes along that time, comparison to known vocal signatures and analysis of other predetermined factors. The data base includes pre-recorded samples of normal and abnormal known pathologies' acoustic signatures pertaining to different parts of the day, different seasons, different stages of the group's development, different species, different breeds, etc. Once an abnormal pathology is detected, the user is alerted. Abnormal signatures, unknown to the system, are being quantified, analyzed and time scaled. Based on statistical formulations, they are ascribed to either known pathologies, new abnormalities or to harmless signatures.

Data analysis may be carried out for each microphone separately, for any group of microphones in specific zones of the house or for the entire set of microphones.

An alert threshold is predefined in the system, based on change parameters (such as quantity and rate) of vocal signatures.

Figure 3A:
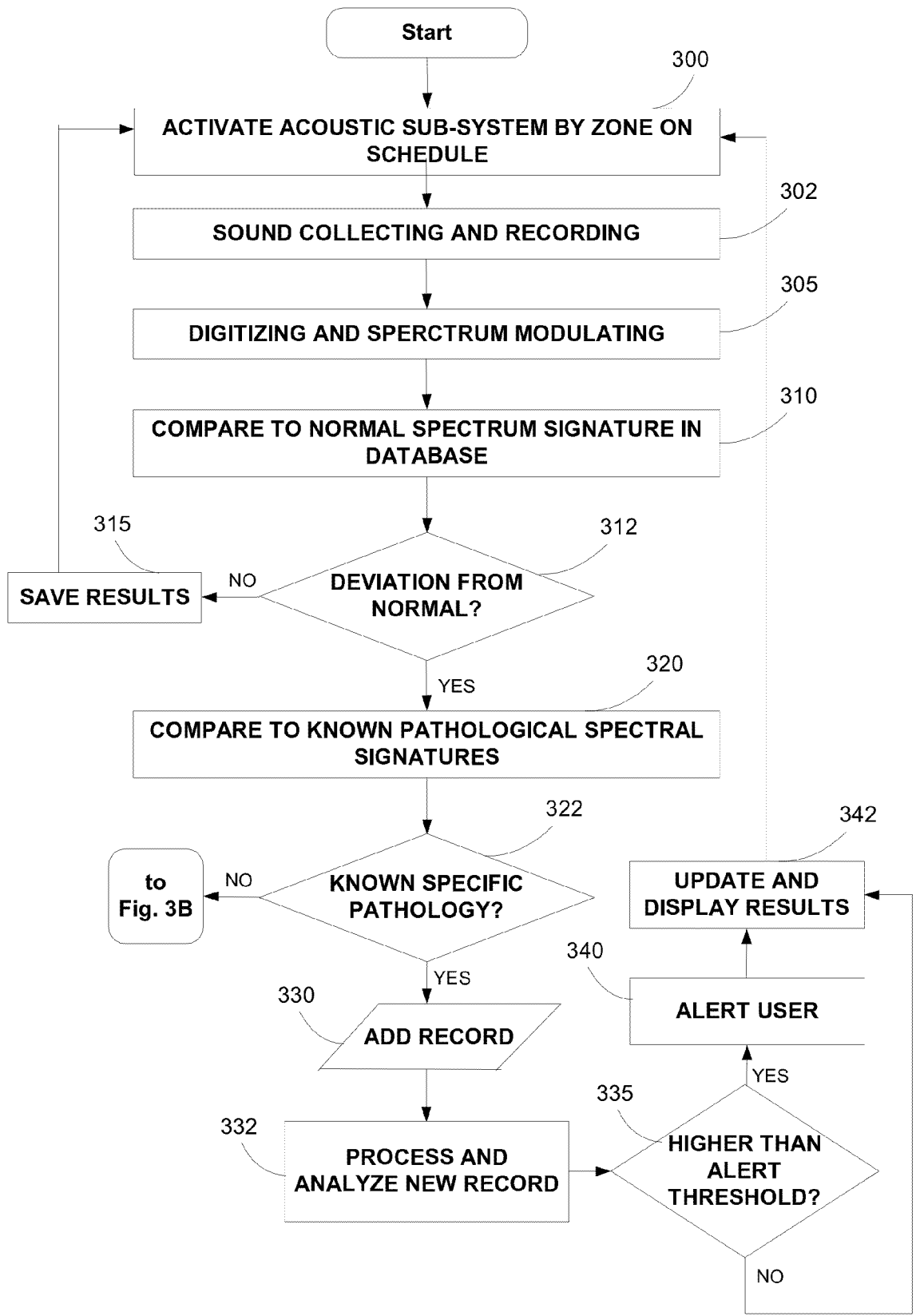
FIGS. 3A and 3B are an exemplary flowchart showing the operation of the acoustic sub-system.
Figure 3B:
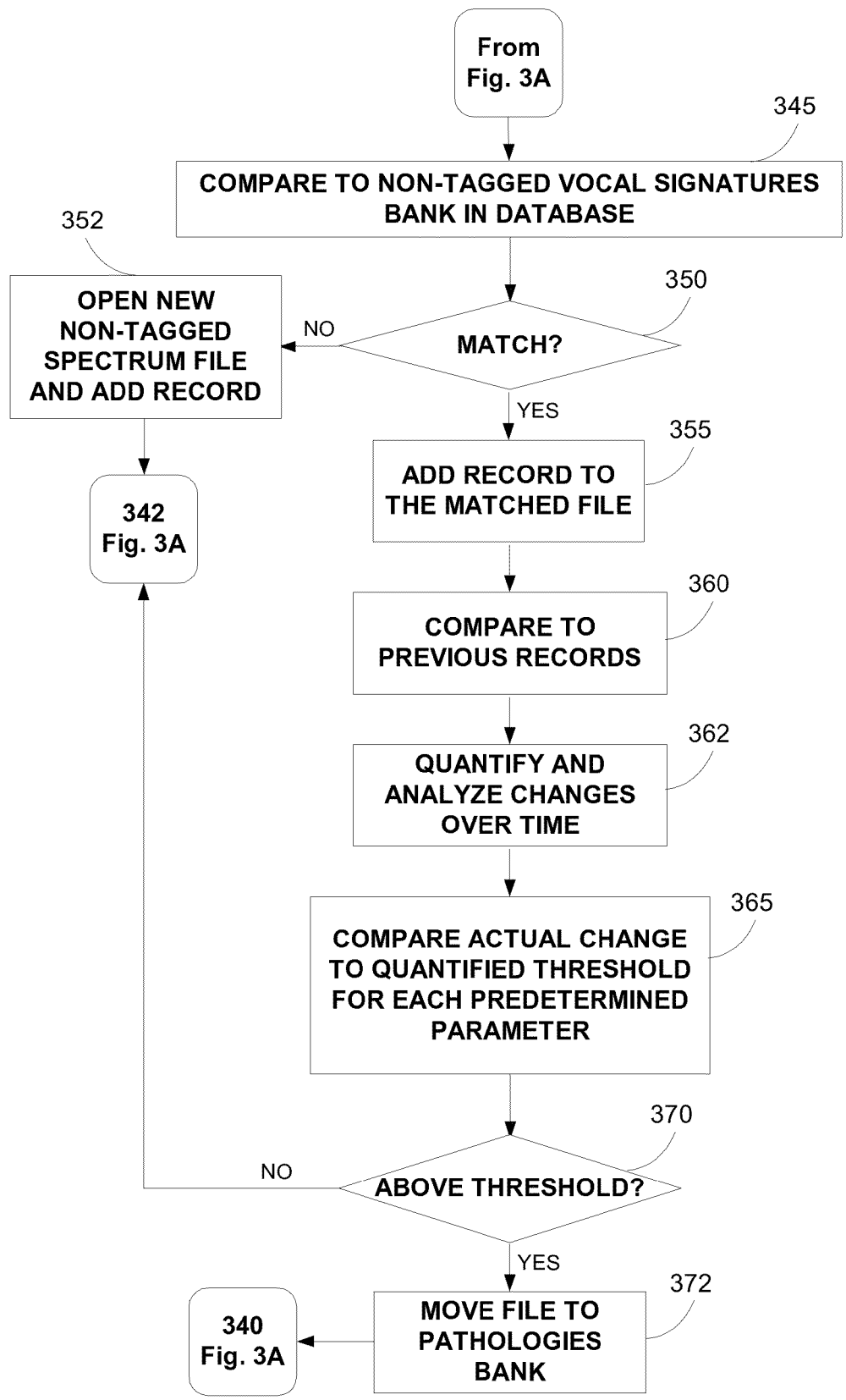

FIGS. 3A and 3B are an exemplary flowchart showing the operation of the acoustic sub-system.

In step (300) the microphones are activated according to the predefined schedule. Sounds are collected and recorded (302), followed by digitization and spectrum modulation (305). The spectrum signature is compared to pre-stored normal spectrum signatures for the present conditions (e.g. region and climate area, time of the year and development stage of the group) (310) and a check for deviation is performed (312).

If no deviation from the normal is detected, the system loops back to scheduled activation (300). Otherwise, the deviating spectral signature is compared to known pathological spectra stored in the database (320). If a match is found, namely the pathology is known (322), a new record is added to the pathology file (330). The new record is processed and analyzed (332), including analysis of data accumulated over a predetermined period, and the resulting quantified parameter is compared to a pre-defined threshold (335). If the result is higher than the threshold the user is alerted (340) and presented with the results (342). The system then resumes scheduled activation. Otherwise, if the result is not higher than the threshold, no alert is issued. If in step (322) it was determined that the spectral signature does not match a known pathology, the system proceeds to compare the signature to non-tagged vocal signatures stored in a separate bank in the database (345, FIG. 3B). If no match is found, namely a similar vocal signature has not been recorded previously, a new non-tagged spectrum file is opened and the new record id added to it (352) and the system proceeds to update the results presented to the user. Otherwise, if a match is found, namely a similar vocal signature has been recorded previously, the new record is added to the matched file (355). The new record is then compared with previous records in the file (360) and changes over time are being quantified and analyzed (362). For each predetermined parameter, a comparison is made between the actual change over time and a predetermined change threshold (365). If it is determined (370) that the change is higher than the threshold, a new pathology is defined and the file is moved to the pathologies' bank (372). The user is alerted and the user interface is updated. Otherwise, if the change does not surpass the threshold, the system updates the presented results.

Ammonia and Scent Sub-Systems

The Ammonia sub-system according to the present invention comprises Ammonia detectors scattered along the site.

Scattering points are chosen and marked on a 3D map of the site, prepared prior to the system's positioning. These detectors are either (a) Wired to the communication center or (b) Include RF transceiver. The detectors are activated separately, by zone groups or all at once. Measures collected are transmitted to the server, detector number and time of collection defined and added to each record. Ammonia level records are digitized and saved. Records are analyzed to detect a raise above predefined threshold level as well as changes indicating disease. The server may be connected to the house operative system and when Ammonia level is above threshold—activate blowers to lower that level. This procedure will be limited to a predefined number of activations. After that, the user will be alerted. Different levels of alert will be activated upon predefined criteria of Ammonia level and change of that level along time.

The scent sensing subsystem according to the present invention comprises scent devices scattered along the site. Scattering points are chosen and marked on a 3D map of the site, prepared prior to the system's positioning. These detectors are either (a) Wired to the communication center OR (b) Includes RF transceiver. Devices are designated to identify specific scents, indicative of specific diseases. They are activated separately, by zone groups or all at once. Measures collected are transmitted to the server, detector number and time of collection defined and added to each record. Fragrance level records are digitized and saved. Records are analyzed to detect a raise above predefined threshold as well as for changes indicating disease status. User will be alerted according to predefined criteria of scent level and change of that level along time.

Figure 4:
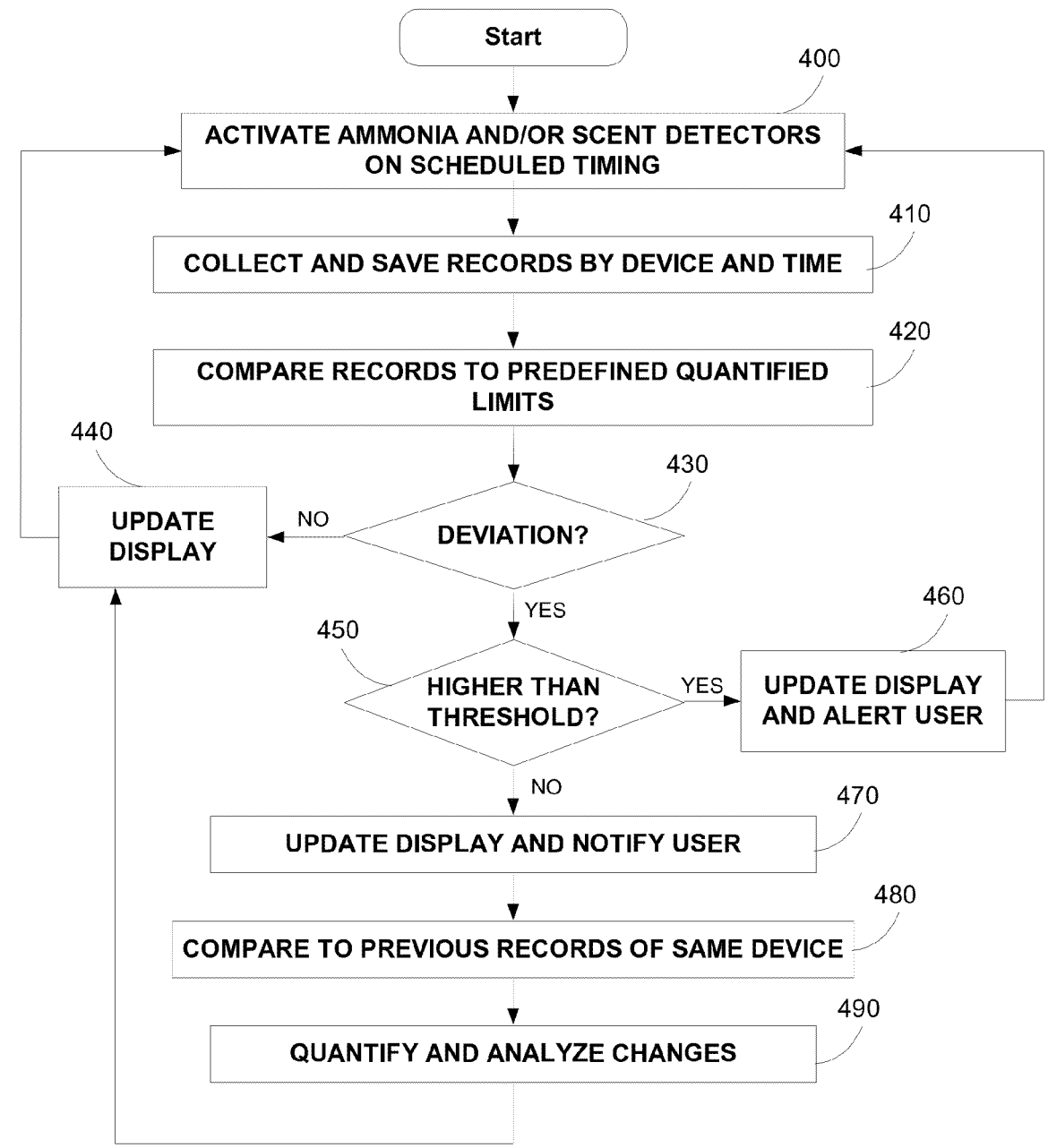
FIG. 4 is an exemplary flowchart showing the operation of the ammonia and scent sub-systems.

FIG. 4 is an exemplary flowchart showing the operation of the ammonia and scent sub-systems.

In step (400) the devices are activated on schedule. Data records are collected and stored by device and time (410) and compared to predefined quantified limits of normal range (420). If no deviation from the limits is detected (430), the system proceeds to update the user's display (440) and resumes scheduled activation. Otherwise, if the records deviate from the predefined limits, the deviation is compared to a predefined threshold (450). If the deviation is higher than the threshold, the user is alerted and the presented results updated (460). If the deviation is not higher than the threshold, the user is notified (470). The current record is then compared to previously stored records of the same device (480) and the changes over time are quantified and analyzed (490). The user's display is updated with the new results (440) and the system resumes scheduled activation.

Vitality Meter Sub-System

The vitality meter sub-system according to the present invention takes the monitoring system from the level of the flock to the level of the individual within the flock.

Figure 7:
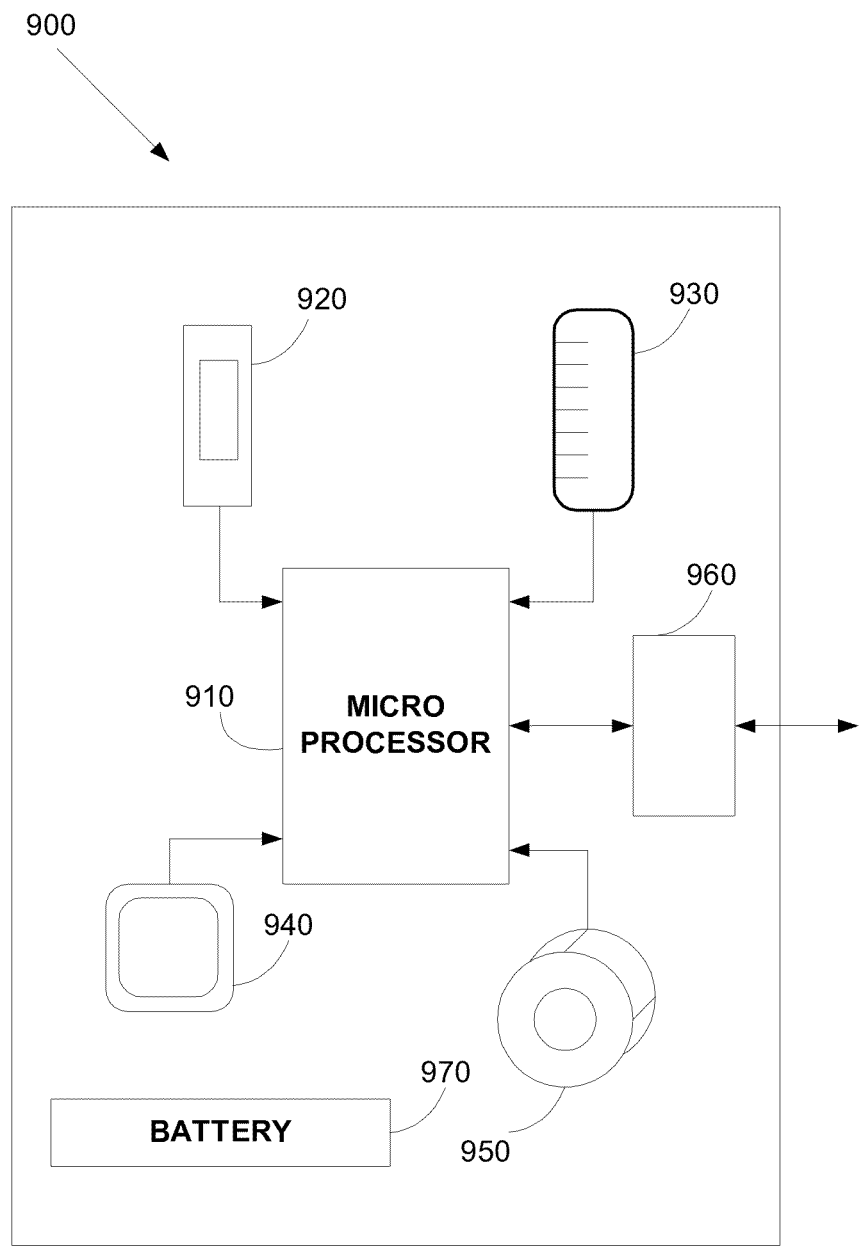
FIG. 7 is an exemplary schematic representation of the vitality meter.

The device comprises one or more of the following components, as depicted schematically in FIG. 7:
a. 3D acceleration measuring component (950) using piezoelectric or MEMS technology.
(Such as: http://wwwdotendevcodotcom/product/ParmProductSearchdotaspx)
b. Pulse rate sensor (920) (Electro-optical or piezoelectric transducer or electromagnetic), such as: Nonin pulse sensor, model 2000SA, http://wwwdotnonindotcom/indexdotasp, or Timex T5 series or Polar FS series, or others.
c. Temperature measuring component (930) using thermistor.
d. Micro-processor (910) of type PIC32 or PIC16 of "MicroChip" or similar.
e. RF receiving and transmitting components (960) such as transponder of type RFID-RADAR, by Trolly Scan Ltd. http://trolleyscandotcom/ or similar, or transceiver of type TRC103 by RFM, http://wwwdotrfmdotcom/indexdotshtml or similar.
g. Power source (970).

The components are integrated to create the vitality meter.

The vitality meter is attached to (or implanted in) a certain number of individuals within the flock, to pre-determined parts of the body—be it a leg, a wing, a neck, or other part. It measures crucial parameters of vitality, all or part of the following: Movement patterns, including differentiation between walking, eating, drinking, standing, sitting, etc., abnormal movements, blood pulse, temperature, rumination and breathing patterns. These parameters are measured continuously or alternately, on a predetermined time scale and the data is collected and transmitted to the system server by means of local RF transmitter. Each unit has its own ID code to enable individual identification of the unit carrier—sentinel.

The vitality meter units are mounted on a sample of statistically sufficient number of individuals within the flock, in order for the data collected to be statistically valid and sufficient for evaluation of the flock's health and for alert of disease outbreak and morbidity rate.

As mentioned above, the "sentinels" (individuals within the flock to which the units are attached) are sampled in a statistically sufficient number, not only to indicate a disease in the specific sentinel but to indicate tendencies of diseases to spread in the entire flock.

Since each "sentinel" has a personal ID through its unit's code and/or local positioning means, it can be easily approached for further investigation and disease diagnosis by the veterinarian.

The local positioning means (940, FIG. 7) may comprise:
a. Radio operated, marked on the systems' 3D map and can consequently be located by the system visual camera or human, and/or:
b. Visually or vocally noted, producing a special signal like a beacon when activated. Signal may be produced by electromagnetic marking devices such as a LED or a piezoelectric buzzer that can be noted/observed at the designated distance and/or:
c. Constantly visually marked and can be observed at any time. Marking is achieved by a ribbon or patch of any material, or other object, attached to any body part of the sentinel and divided to symmetric areas, each with a different color. The combination of colors on the marker defines the sentinel's ID, hence enabling individual visual monitoring of the sentinel by camera or by human eyes.
d. Local Positioning System (LPS), implementing GPS technology on a local scale.

When a specific transceiver or transponder transmits its ID code, the transmission is received by a plurality of receivers scattered in the site. The server calculates distance from the receiving antennae according to the time differential of the received transmissions and the combined distances mark the sentinel's position.

All data transmitted from the sentinels is stored and analyzed at the system server, compared to data from other sensors and to healthy normal range of parameters. The analyzed data may be presented in charts and graphs and the system alerts the user of any abnormality.

Alerts are made to the farmer/veterinarian—according to predetermined criteria—to their mobile phone, PC, laptop or any other instrument of their choice.

Figure 5A:
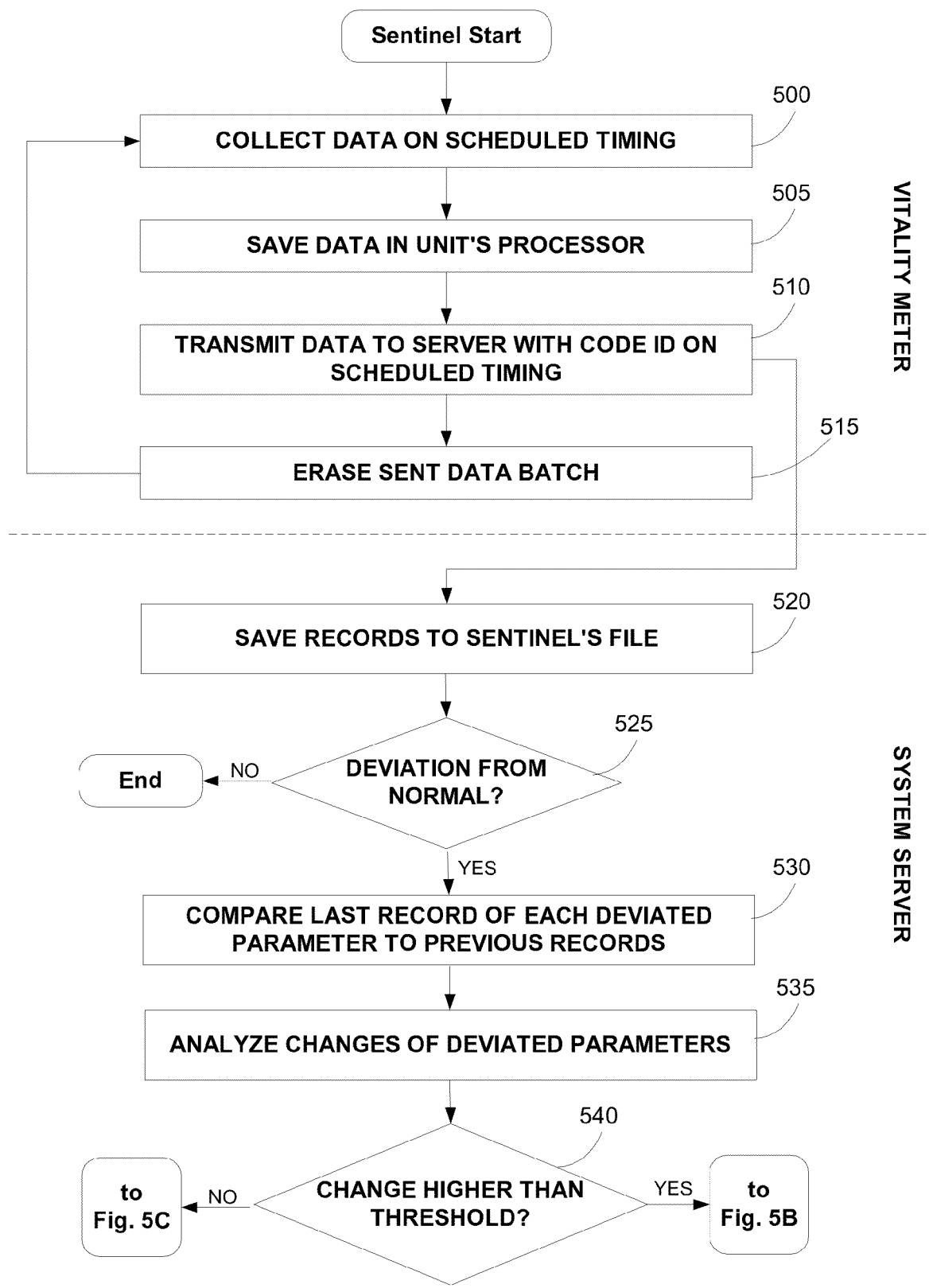
FIGS. 5A through 5C are an exemplary flowchart showing the operation of the vitality sub-system.
Figure 5B:
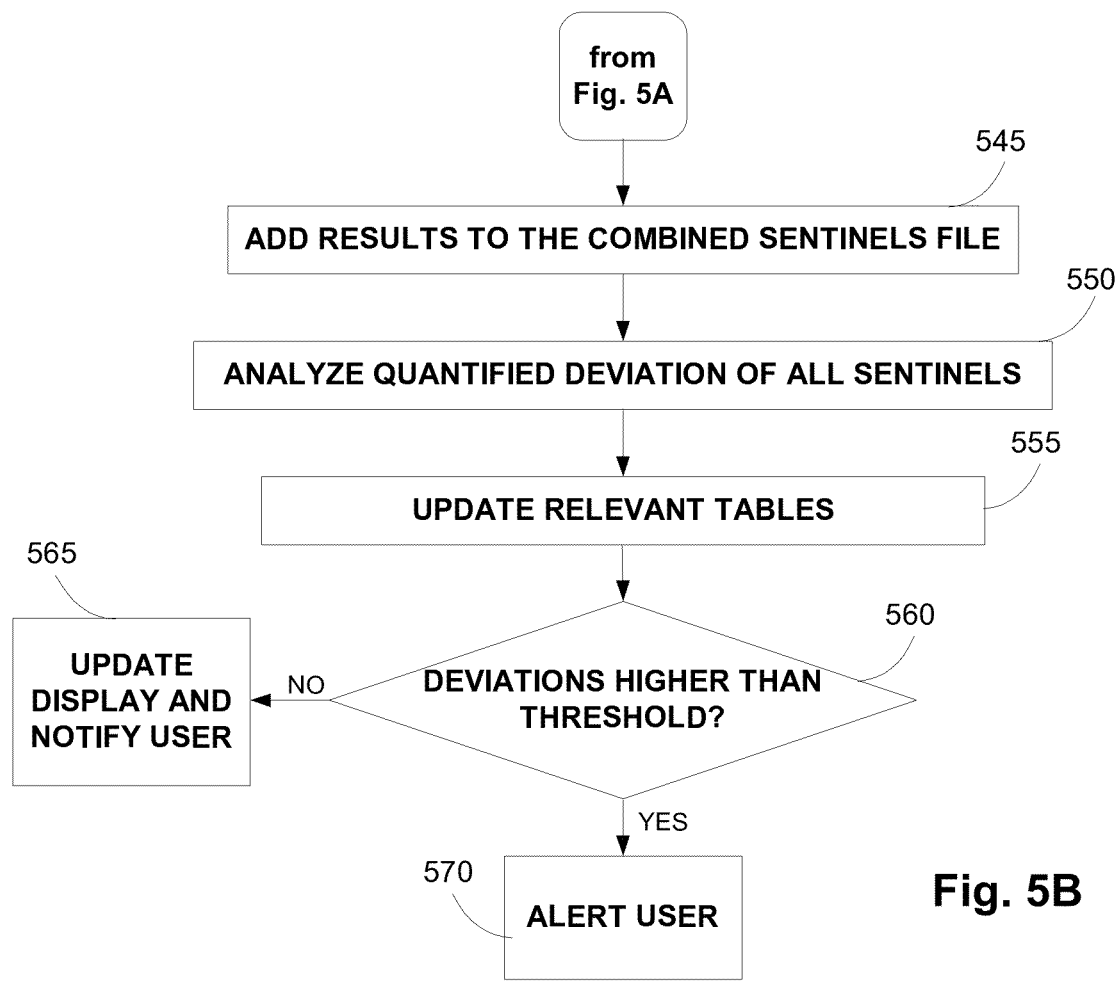
Figure 5C:
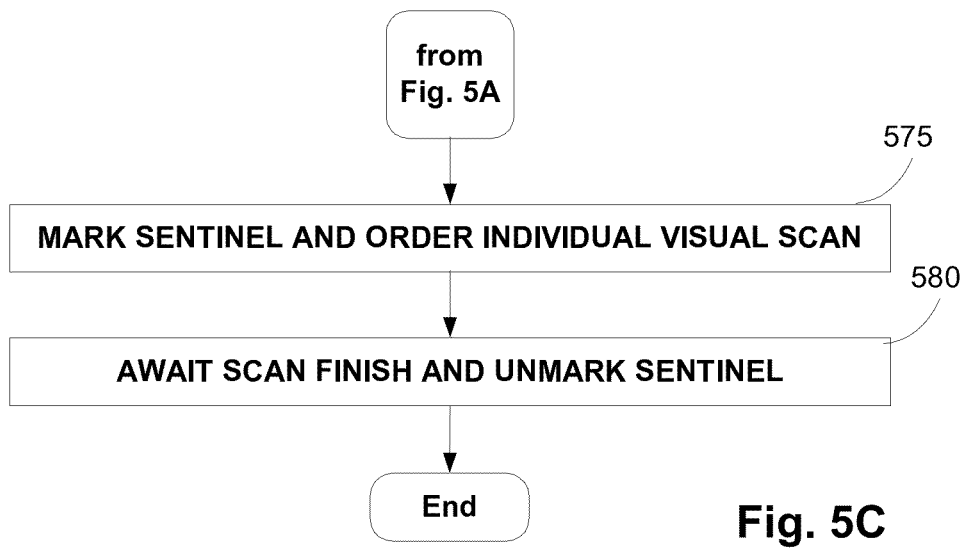

FIGS. 5A through 5C are an exemplary flowchart showing the operation of the vitality sub-system. The flowchart represents operations relating to a single sentinel, where identical processes are simultaneously taking place for all sentinels.

In step (500) data is collected from the sentinel's vitality meter and temporarily saved in the vitality unit's processor memory (505). Subsequently, on scheduled timing, the stored data is transmitted to the system server (510) and then erased from the unit processor's memory (515).

On the server side, the received records are saved (520) and each parameter is checked for deviation from its predefined normal range (525). If no deviation is detected, the operation ends till the receipt of a subsequent batch of data. Otherwise, if a deviation from normal is detected for any of the parameters, the last record for each deviating parameter is compared with its previous records (530) and the changes are analyzed (535). The changes in parameters are compared to individual thresholds (540). If the change is determined to be higher than the threshold, the results are added to a combined sentinels file (545, FIG. 5B), the quantified deviations of all the sentinels for each specific parameter are analyzed (550) and the relevant database tables are updated (555). The aggregate deviation is then compared to a predefined threshold (560) and an alert is issued to the user (570) if the threshold has been surpassed. Otherwise, the user is notified of the changes.

If the changes in the parameters of the individual sentinel are not higher than the threshold, the sentinel is marked (in the database) and an individual visual scan is ordered from the visual subsystem (575, FIG. 5C), using the sentinel ID and/or position marker. Upon completion of the individual visual scan, the sentinel is unmarked (580).

Visual Sub-System

The visual sub-system according to the present invention combines both capabilities of the system—group and individual monitoring. The sub system comprises digital cameras scattered along the site. Scattering points are chosen and marked on a 3D map of the site, prepared prior to the system's positioning. These cameras are either (a) Wired to the communication center or (b) Includes RF transceiver. They are activated separately, by zone groups or all at once. Visual data collected is transmitted to the server, camera number and time of collection defined and added to each record. Records are modulated, then processed and analyzed as described in conjunction with FIG. 6. Process includes (but is not limited to) quantification and manipulation of digitized data along a time scale, analysis of changes along that time, comparison to known visual patterns and analysis of other predetermined factors. The database includes pre-recorded samples of normal, abnormal, and known visual representations of pathologies and behavior patterns. Once an abnormal pathology is detected, the user is notified or alerted according to predefined criteria. Abnormal patterns, unknown to the system, are being quantified, analyzed and time scaled. Based on statistical formulations, they are ascribed to either known pathologies, new pathologies or to harmless patterns.

Data analysis may be carried out for each camera separately, for any group of cameras in a specific zone of the house or for the entire set of cameras.

A threshold of alert is predefined in the system, based on change parameters (such as quantity and rate) of visual signatures.

When a specific camera observes an abnormal pattern demonstrated by one (or more) of the individuals, it automatically zooms on that individual and tracks it for a predetermined period of time, before returning to the normal scanning routine.

On top of scheduled scanning, cameras perform specific scanning or zooming and tracking when scheduled for this task by the system, consequently to discovery of abnormal patterns by any other sub-systems, as described in detail in conjunction with FIG. 6.

Further to these assignments, the visual sub-system may be assigned to perform individual vitality monitoring and tracking. In this mode, each camera covers a limited and specific zone of the house. The camera will track all marked sentinels that are within its zone for a predefined time scheduled for this assignment. Sentinels movement characteristics and details will be recorded and saved to each sentinel personal file and further analyzed as described in conjunction with the vitality subsystem.

FIGS. 6A through 6F are an exemplary flowchart showing the operation of the visual sub-system.

In step (600) the system checks whether a request for focused scan is pending. If it is, the system proceeds to step (650, FIG. 6B) to perform a focused scan. Otherwise, the visual zone scan is activated by scanning the first defined zone, zone "0", for a predetermined period (610), followed by incrementing the scanned zones count (615). The scan results are compared to pre-stored abnormality files (620) and if abnormalities are detected (625) the system proceeds to step (650, FIG. 6B) to perform a focused scan. If no abnormalities were detected, the system checks whether all the zones have been scanned (630). If more zones need to be scanned, it proceeds to the next zone (635). Otherwise, if all zones have been scanned, the scanned zones count is zeroed and the system proceeds to step (735, FIG. 6D) to perform sentinels scan.

In step (650, FIG. 6B) a focused scan is activated, for the first requested zone or sentinel and the scan record is saved (660). The record is compared to normal pattern files stored in the database (665) and if the comparison shows normal patterns (670) the system loops back to step (600, FIG. 6A). Otherwise, if an abnormal pattern was detected, which does not belong to a known pathology (675), the system proceeds to step (705, FIG. 6C) for analysis. If the abnormal pattern detected is that of a known pathology, the present record is compared to previously stored records (680). The changes (from previous records) of each pathology are quantified and analyzed (685), analysis results saved and user display updated accordingly (690). If the changes are above a predetermined limit (695), the user is alerted (700). The system loops back to step (600 FIG. 6A).

In step (705, FIG. 6C) the abnormal parameters of an unknown pathology are quantified (as per their deviation from normal) and analyzed. A new abnormality file is added to the database (710) with the records and analysis results. The system then notifies the system engineer to incorporate the detected abnormality to a new category in the system (715) and the user's display is updated with the new results (720). If the change is above a predefined threshold (725) the user is alerted (730). The system loops back to step (600 FIG. 6A).

Figure 6A:
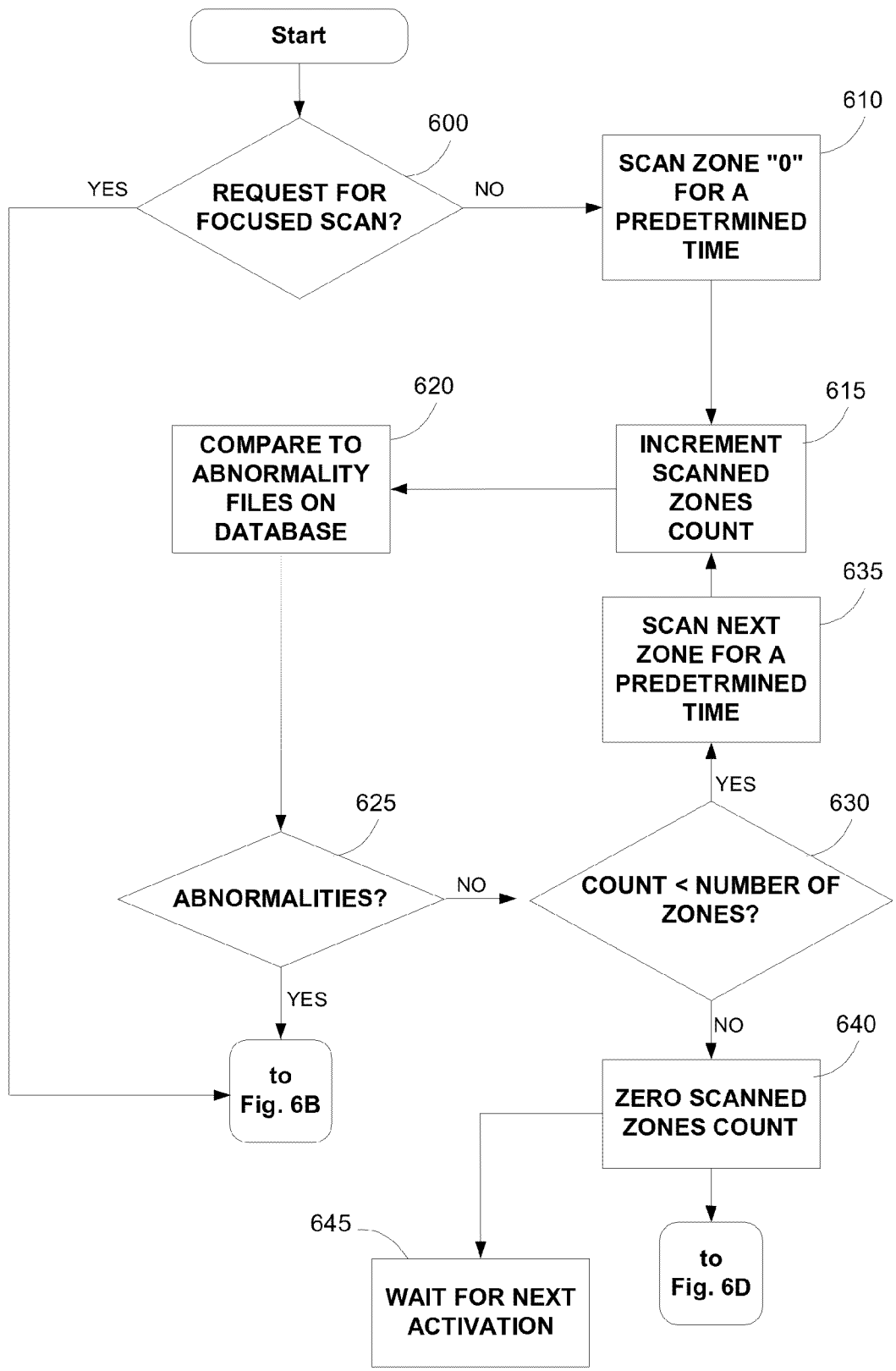
FIGS. 6A through 6F are an exemplary flowchart showing the operation of the visual sub-system.
Figure 6B:
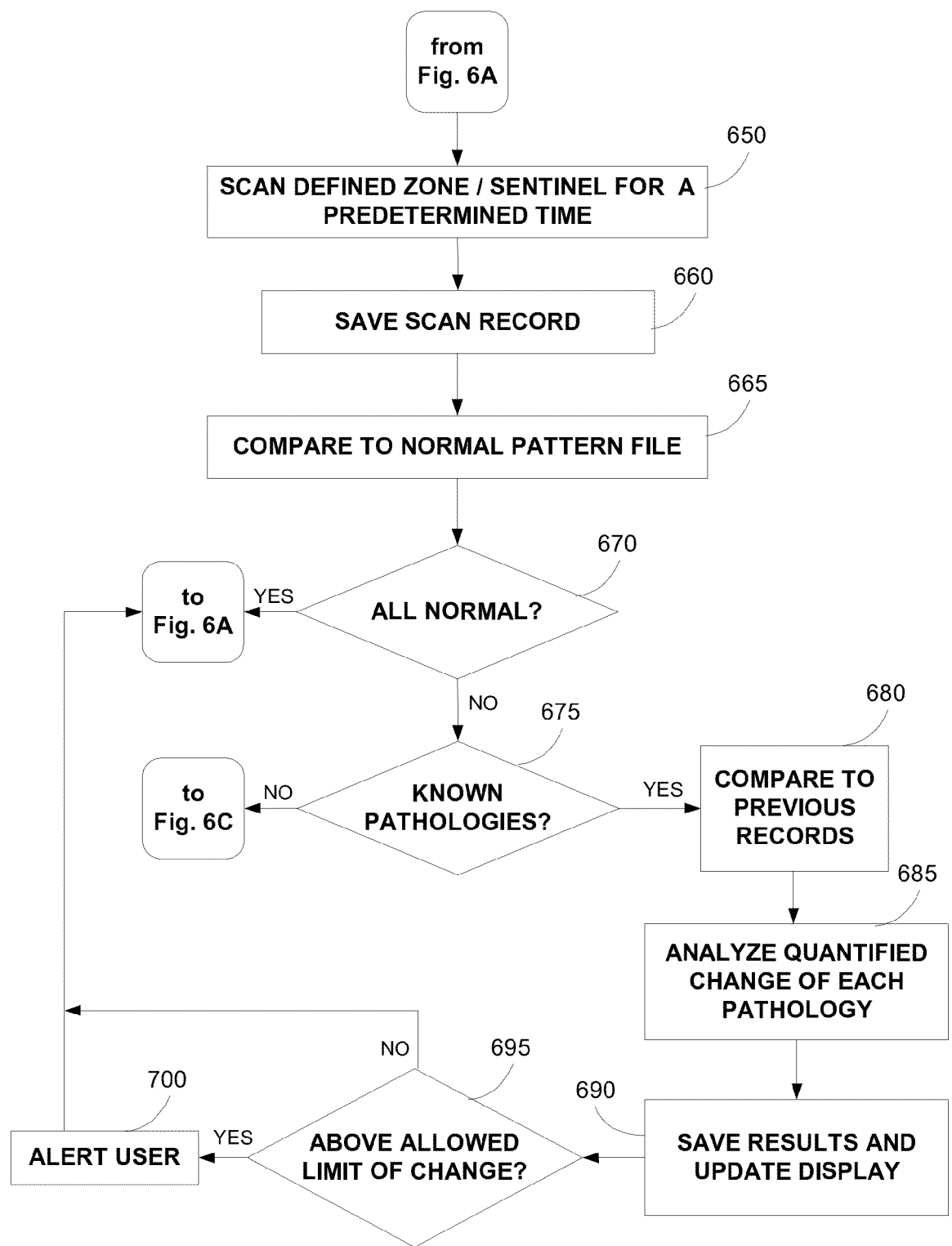
Figure 6C:
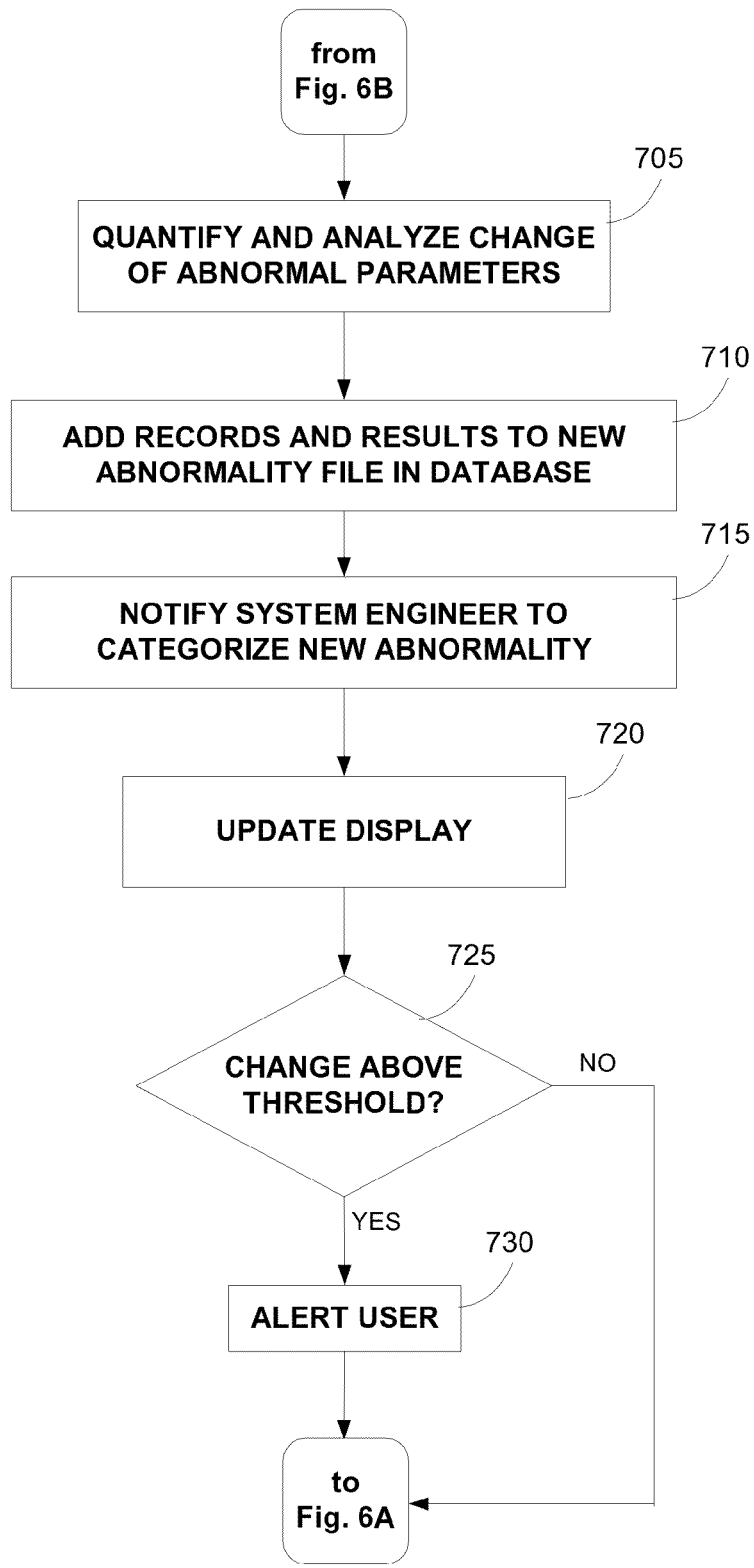
Figure 6D:
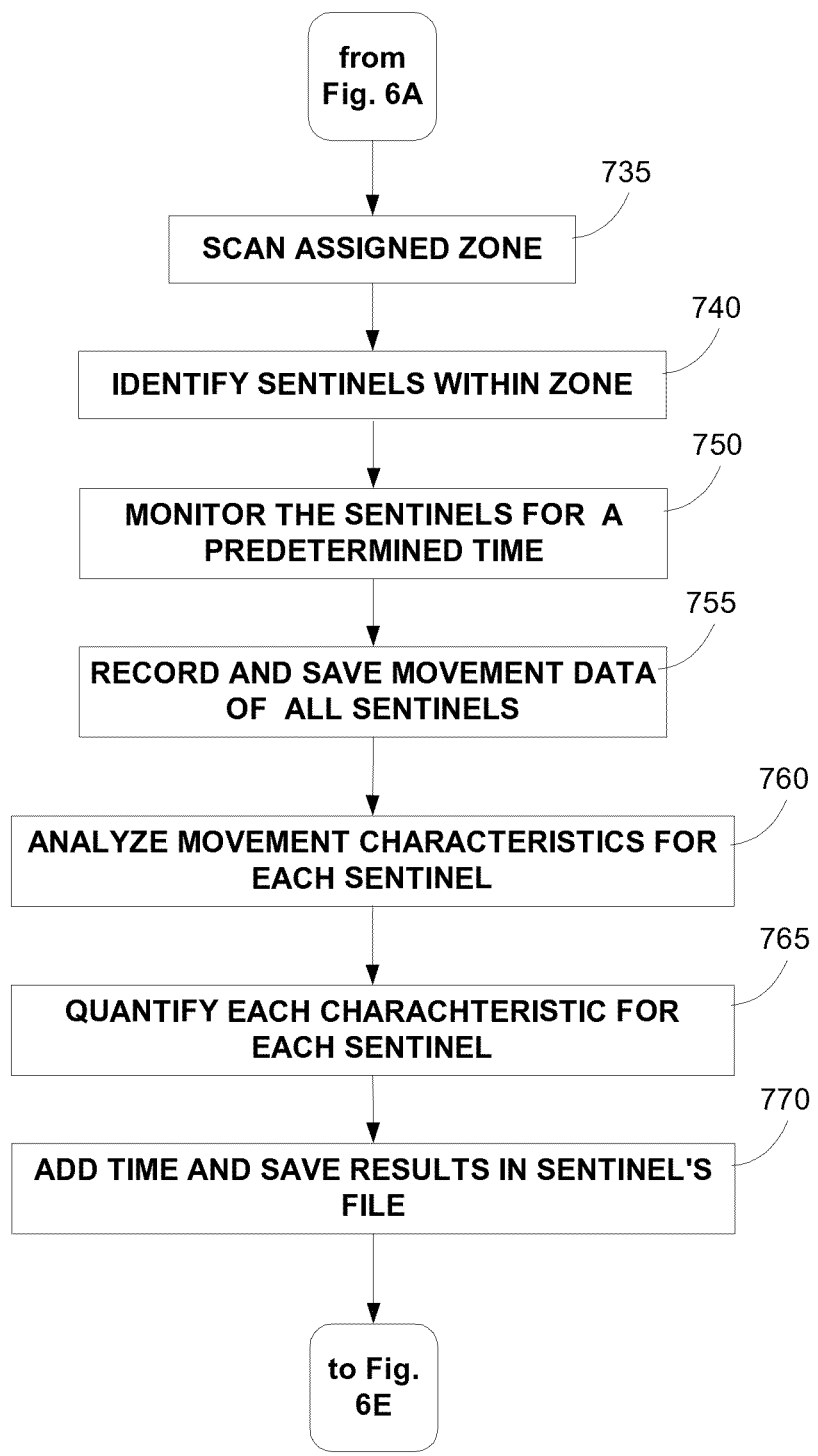
Figure 6E:
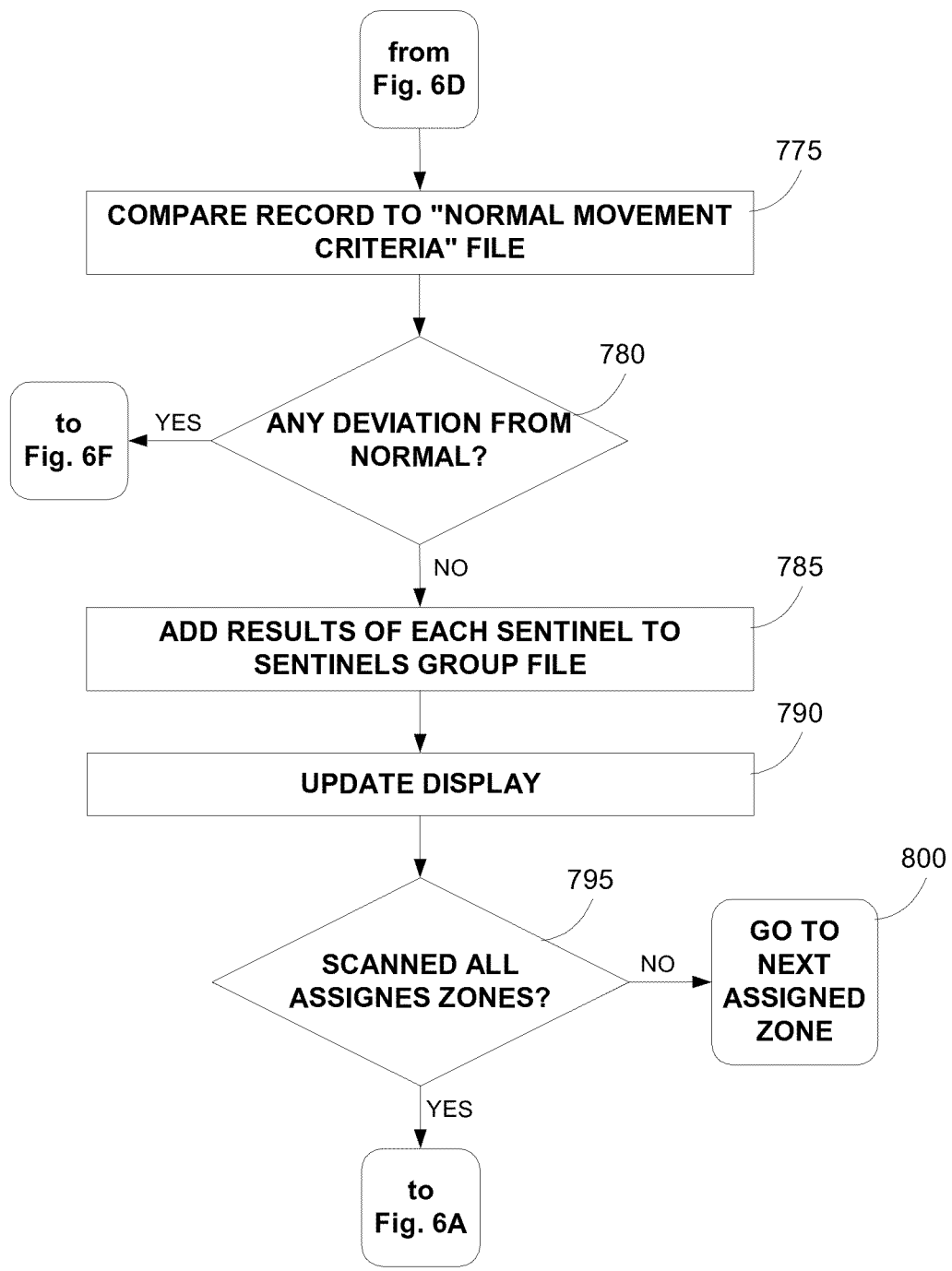
Figure 6F:
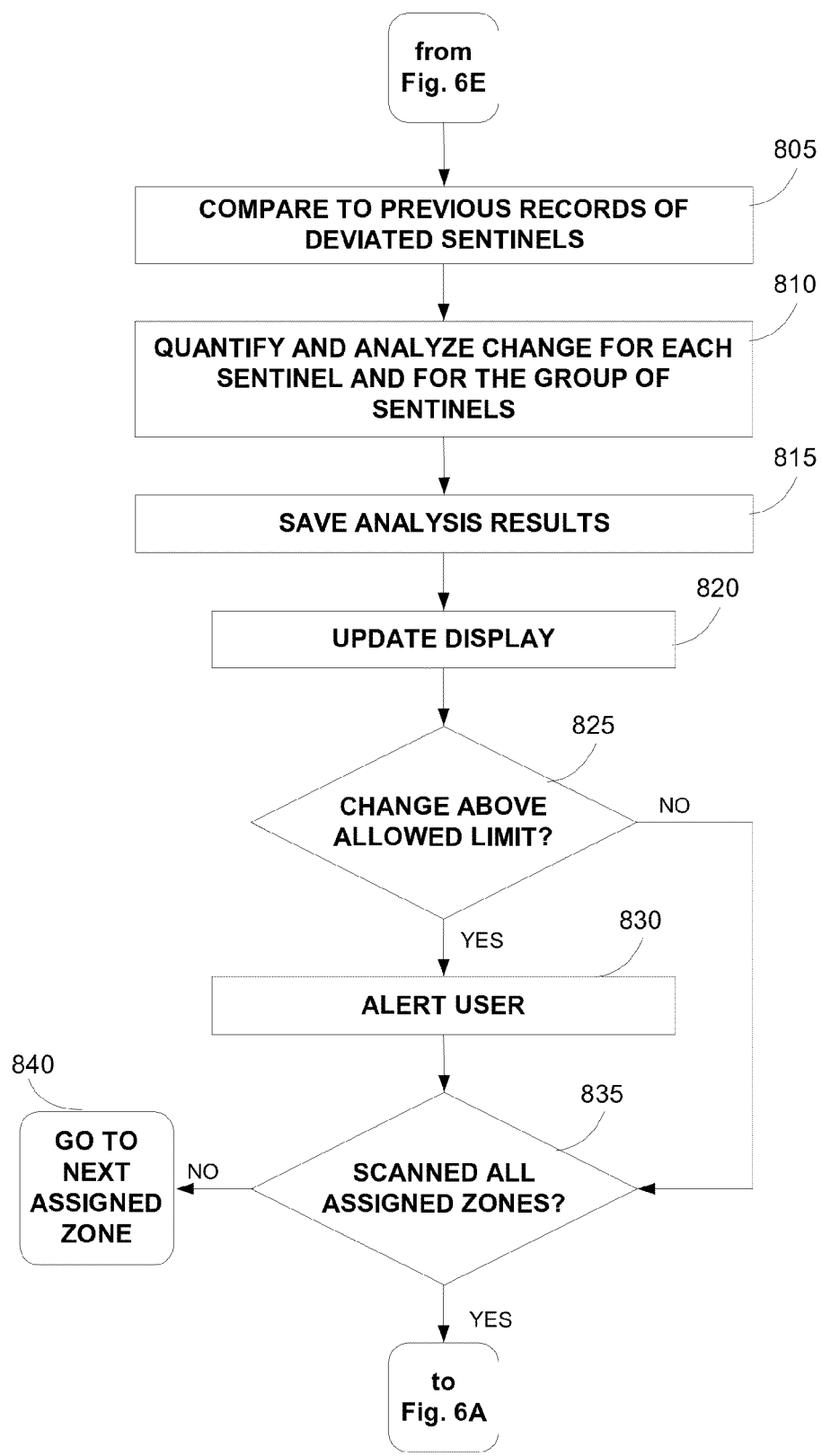

In step (735. FIG. 6D) the sentinels scan is activated by scanning the assigned zone. The sentinels are identified within the scanned zone (740), as described above and the system proceeds to monitor the identified sentinels for a predetermined time (750). During the monitoring period, movement data of all the monitored sentinels is recorded and saved (755). Following the monitoring period, the saved records are analyzed for movement characteristics, for each sentinel (760). Each detected characteristic is quantified (765) and the results are saved in the sentinel's file, with a timestamp (770).

In step (775, FIG. 6E) each sentinel's record is compared to a pre-stored file defining normal movement criteria. If a deviation from normal is detected (780), the system proceeds to step (805, FIG. 6F) for analysis. Otherwise, if all the sentinels' movements are deemed to be normal, the sentinel group file is updated with the individual results of each sentinel (785) and the user display is updated (795). If all the requested zones or sentinels have been focus-scanned (795), the system loops back to step (600 FIG. 6A). Otherwise, a focus scan is initiated for the next requested zone or sentinel (800).

In step (805, FIG. 6F) the deviated sentinel's record is compared to previous records of deviated sentinels. The changes for each sentinel and for the group of sentinels are quantified and analyzed (810), the analysis results are saved (815) and the user's display is updated (820). If the detected change is above a predefined limit (825) the user is alerted (830). If all the requested zones or sentinels have been focus-scanned (835), the system loops back to step (600 FIG. 6A). Otherwise, a focus scan is initiated for the next requested zone or sentinel (840).

Existing in-House Devices

The server of the present invention may be connected to existing infra structures of the poultry house. Data collected in these devices is added to the database and used by the system to analyze and evaluate the flock's health status—continuously.

Data may include feeding and watering rates, house temperature and humidity, weighting results of chickens in the house (randomly taken) or any other factor currently measured in the operative system of the poultry house.

Workflow Example

Following is an exemplary workflow of the system according to the present invention, for detecting Infectious laryngotracheitis (ITL) in poultry.

ITL is an acute, highly contagious, herpesvirus infection of chickens and pheasants characterized by severe dyspnea, coughing, and rales. It can also be a subacute disease with lacrimation, tracheits, conjunctivitis, and mild rales. It has been reported from most areas of the USA in which poultry are intensively reared, as well as from many other countries.

Clinical Findings: In the acute form, gasping, coughing, rattling, and extension of the neck during inspiration are seen 5-12 days after natural exposure. Reduced productivity is a varying factor in laying flocks. Affected birds are anorectic and inactive. The mouth and beak may be bloodstained from the tracheal exudate. Mortality varies, but may reach 50% in adults, and is usually due to occlusion of the trachea by hemorrhage or exudate. Signs usually subside after approximately 2 weeks, although birds may cough for 1 month. Strains of low virulence produce little or no mortality with slight respiratory signs and lesions and a slight decrease in egg production.

In the workflow of the system according to the present invention, respiratory signature changes are the first to be detected by the acoustic sub system—within hours from first appearance of clinical signs. Upon activation (205) of the acoustic sensors—data is recorded (302), digitized and modulated (305). Upon comparing this record with normal spectrum signature file (310) on the data base, a deviation from normal is detected (312). Rales (The digitized signature of the pathology is preprogrammed to the system's data base) are increasingly overheard, especially at night sessions, when other daily vocal signatures are silenced. Same patterns will be evident for other pathologies such as coughing and gasping. Records are analyzed (332) and compared to predefined allowed limits of the quantified pathology (335). Analysis is preformed for both the quantified phenomenon in itself (level/volume of rales/coughing/gasping signature in its spectrum band) and for the rate of change of each phenomenon. If it is higher than threshold (i.e.: a large number of birds are having the symptom and/or rate of manifestation is high) (335), an alert will be triggered by the subsystem (340). If lower than threshold, updates are made (342) and the subsystem returns to routine.

In itself, if the rate of pattern change of the acoustic pathologies is high enough it will trigger an alert.

The Vitality sub-system will produce indications following (or simultaneously) to the acoustic sub-system. Once activated, (500) an increasing number of infected sentinels will exhibit a continuous decrease in productivity, feeding and activity (545). In itself, if the number of sentinels exhibiting a decrease in vitality patterns is above predefined threshold for each parameter, it will trigger alert. The rate of change is also analyzed and may trigger an alert for fast deterioration of vitality even for a relatively small number of sentinels (550). Criteria for alert are preprogrammed for each parameter measured as well as for change rate.

Visual indication: Ordered specific focused scan of zone or of sentinels (575/600/650) will identify the extension of the neck during inspiration (predefined as a pathology) (675) of these sentinels.

Existing infrastructure systems: Data from these systems will indicate (230) a decrease in water and food consumption, respectively to the changes indicated in other subsystems.

Even if alert is not triggered by any specific subsystem, it may be triggered by the system's program, based on the statistical weight of indicating parameters and on the rate of change of these parameters along a predefined time scale.

For example: The disease is in early stages and not many sentinels have been infected.

However, acoustic changes and visual observations of extended necks are growing by the hour. The system will trigger an alert.

The following table is an exemplary system alert determination schedule based on the various sub-systems' indications.

| Disorder (Samples) | Subsystem | | | | | | System Alert Level |
|---|---|---|---|---|---|---|---|
| | Vitality | Acoustic | Ammonia | Visual | Feeding | Water | |
| Heat stress | Sharp decrease in movement - all sentinels | Decrease at all frequencies | Mild increase | No change | High decrease | High increase | |
| AL | 5 | 5 | 1 | 0 | 5 | 5 | 5 |
| Cold stress | Mild decrease in movement - all sentinels | No change | No change | No change | High increase | High decrease | |

-continued

| Disorder (Samples) | Subsystem | | | | | | System Alert Level |
|---|---|---|---|---|---|---|---|
| | Vitality | Acoustic | Ammonia | Visual | Feeding | Water | |
| AL Chronic Disease (e.g. Coccidiosis) manifestation | 2 Mild decrease in movement - growing % of sentinels | 0 No change | 0 Low to medium increase | 0 Growing visual signs | 2 Moderate decrease | 2 Moderate decrease | 3 |
| AL Acute Disease (e.g. Avian Flue, Newcastle) manifestation | 3 Fast decrease in vitality - in a fast growing number of sentinels | 0 | 3 Fast growing patterns of pathologies signatures | 1 Rapid increase | 2 Visual pathologies | 2 Mild decrease | 4 |
| | | | | | Mild decrease | | |
| AL Chronic respiratory disease | 5 Moderate decrease in vitality - in a moderately growing number of sentinels | 5 Moderately growing patterns of pathologies signatures | 5 No change | 4 Moderate growth of visual pathologies | 1 Mild decrease | 1 No change | 5 |
| AL Acute respiratory disease (e.g. ILT) | 4 High decrease in vitality - in a highly growing number of sentinels | 4 High rate of growing patterns of pathologies signatures | 0 None to mild increase | 3 Rapid growth of visual pathologies | 1 Moderate decrease | 0 Moderate decrease | 4 |
| AL | 5 | 5 | 2 | 4 | 1 | 1 | 5 |

Legend:
Alert Level (AL) 0: Normal state, healthy productive flock.
Alert Level (AL) 1: Mild disruption, slight decrease in productivity.
Alert Level (AL) 2: Mild disruption, slight decrease in health status. Notify user.
Alert Level (AL) 3: Mediocre disorder. Low level alert.
Alert Level (AL) 4: Significant disorder. High level alert.
Alert Level (AL) 5: Catastrophe. Emergency alert.

The technology described above refers mainly to poultry but is well applicable to other livestock groups—with proper modification for each species monitored.

Exemplary Implementation to Other Species:

Bees and Bee Hives:

The main three units of the system remain, i.e.: Sensors array, communication platform and computing unit. Modified elements at each unit:

1. Computing unit (System server): Data base and software, corresponding and designed to bees health factors, disease, productivity etc. Operating software is modified respectively.
2. Sensors array. Sensors that are scattered in the hive or its door or nearby the hives, collecting data from a sample of statistically sufficient number of hives within the group. Array may include (but not limited to) the following:
   (a) Acoustic sensors. Microphones or other acoustic sensors. A healthy hive can be characterized by certain acoustic patterns, typical for each sub-specie, time of day, season and development stage of the colony. These patterns are changing in accordance with the nature of activity and its extent, correlative to the colony's health. Changes of acoustic patterns may be indicative of the hive general health, and in some cases, even of high probability for specific disease, such as Chronic Paralysis or Nosema, that are characterized by rapid and dramatic reduction of activity within the hive.
   (b) Scent sensors. Dedicated sensors for specific scents, typical of certain diseases, such as AFB and EFB. These diseases are characterized by unique odor which increases correlatively to its infestation.
   (c) Weighting scales. Indicative of the colony production rate, general health and its development status and rate.
   (d) Temperature sensors. Indicative of the colony production rate, general health and its development status and rate.
   (e) Visual sensors. Video camera/s collecting visual information from each apiary door and the immediate vicinity of the door. Some bees disorders such as Chronic paralysis, Nosema and Tracheal Mites have typical visual symptoms that may be observed mainly at the entrance to the hive or near by.
3. Communication center, located on site, no modification is required.

Additional power source is required for this application, adequate for operation in outdoor conditions.

Grazing Herds of Sheep or Cattle:

The system is applicable to large herds of grazing sheep, goats or cattle. These herds are kept outdoors all year around and are inspected as a group—with no individual monitoring of each and every member of the group. Inspection usually takes place in gathering points—where the herds come for drinking or for supplemental food supply. This farming pattern is very common in South America, in the south west of the US, in Australia and in New Zealand (with sheep).

Again, the main three units of the system remain, i.e.: Sensors array, communication platform and computing unit. Modified elements at each unit:

1. Computing unit (System server): Data base and software, corresponding and designed to cattle/sheep health factors, disease, productivity etc. Operating software is modified respectively.
2. Sensors array. Array may include (but is not limited to) the following:
   (a) Vitality sensors modified for cattle/sheep, implanted in or attached to a sample of statistically sufficient number of individuals/sentinels within the herd. Such units as commercially used for dairy herds, like "Afi-Act" of S.A.E. Afikim (wwwdotafimilkdotcodotil/) or similar, with proper modification in the radio component of the unit.
   Vitality signs are indicative of most of the cattle and sheep diseases and disorders (Anaplasmosis, BVD, Foot and mouth—to mention just a few). A change in walking pace, a limp, a decrease in rumination rate and temperature change are all signs of some disorder. Early detection of these signs is made possible by the vitality unit. In case the unit is implanted, an additional amplified transceiver will be attached to the sentinel's neck for transmission of the sentinel's vitality data collected to the communication center.
   (b) Visual sensors. Video camera/s, located in the above mentioned gathering points, collecting visual information on the sentinels and herd at gathering times. Some cattle and sheep disorders such as: Blackleg, bloat, BVD, Foot rot, Listeriosis and others have typical visual patterns that may be observed and analyzed by the system. Together with the cumulated data of the vitality units of the sentinels, the visual data may focus the analysis and display probability for specific disorders.
   (c) Acoustic sensors. Sensors scattered along the gathering site, collecting vocal data of the herd (abnormal breathing, coughing, stress or others). Data is communicated to the communication center located on site by means of local RF transceivers or local wiring. Vocal data may indicate diseases such as: Anaplasmosis, Anthrax, Thrombosis, TB, Rinderpest and others.
3. Communication center. Modification for this application may include long range radio transceiver, for remote rural areas in which cellular infrastructure does not exist and additional rechargeable power source, possibly with solar charger for long term operation.

The invention claimed is:

1. A system for detecting a health condition of a group of livestock comprising:
   a sensor that measures a vitality parameter value for a group of sentinels, said group of sentinels comprising a statistically significant sample of the group of livestock;
   a processor that:
       assesses a health status of said group of sentinels based on said vitality parameter value;
       tracks and records a record of said health status over time; and
       detects the health condition of the group of livestock based on said record, and
   a data storage unit that stores a datum related to at least one item selected from the group consisting of an output of said sensor, said vitality parameter value, said health status, said record and said health condition;
   wherein said processor further identifies one or more individuals from said of sentinels, and wherein said sensor further measures a respective individual value of said vitality parameter value for each of said one or more individuals;
   wherein said one or more individuals include at least one animal selected from the group consisting of poultry in a poultry house and fish in a fishpond.

2. The system of claim 1, further comprising:
   at least one indicator attached to each of said one or more individuals to facilitate identification of each of said one or more individuals.

3. The system of claim 2, wherein said at least one indicator includes at least one device selected from the group consisting of an identifier, an optical beacon, a radio beacon, a location indicator, a marker and a location sensor.

4. The system of claim 1, wherein said processor further monitors a respective individual health status of each of said one or more individuals over time and wherein said record includes said respective individual health status.

5. The system of claim 4 wherein said processor further ranks a plurality of said one or more individuals with respect to at least one item selected from the group consisting of said respective individual value of said vitality parameter value, said respective individual health status and a measured behavior.

6. The system of claim 1, wherein said processor further identifies at least one pattern selected from the group consisting of a change of said vitality parameter value over time, a change in rate of change of said vitality parameter value over time, a change of said respective individual value of said vitality parameter value over time, a change in rate of change of said respective individual value of said vitality parameter value over time, and wherein said processor further tracks said at least one pattern.

7. The system of claim 6, wherein said processor further compares said at least one pattern to a stored value to indicate a status selected from the group consisting of normal, abnormal, pathological and unidentified.

8. The system of claim 1, wherein said processor further monitors a behavior of each said one or more individuals over time based on said respective individual value of said vitality parameter value.

9. The system of claim 1, wherein said processor further quantifies a respective amount of movement of each of said one or more individuals and further assesses said respective individual health status based on said respective amount of movement.

10. The system of claim 1, wherein said processor further analyzes said respective individual value of said vitality parameter value of each of said one or more individuals to indicate a tendency of a disease to spread in the group of livestock and wherein said health condition is detected based on said tendency.

11. The system of claim 1, wherein said processor further analyzes a disorder level based on a percentage of sentinels indicating a decrease in said health status and wherein said record further includes said disorder level, and said processor detects the health condition of the group based also on said disorder level.

12. The system according to claim 1, wherein said sensor includes a digital camera and wherein said digital camera covers a specific zone, and said processor identifies an individual from said group of sentinels in said specific zone.

13. The system of claim 1, wherein said processor further quantifies at least one factor selected from the group consisting of said health status of the group, said vitality parameter value, said respective individual value of said vitality parameter value, a change in said health status of the group, a rate of change of said health status of the group, a change in said vitality parameter value, a change in said respective individual value of said vitality parameter value, a rate of change of said vitality parameter value, a rate of change of said respective individual value of said vitality parameter value, a behavior each of said one or more individuals, a change in a behavior of each of said one or more individuals, and a rate of change of a behavior of each of said one or more individuals and wherein said processor further compares a result of said quantifying to at least one item from the group consisting of a stored value, a statistic derived from said vitality parameter value, a statistic derived from said respective individual value of said vitality parameter value, a statistic derived from a previously measured respective individual value of said vitality parameter value, and a statistic derived from a previously measured vitality parameter value.

14. The system of claim 1, wherein said processor further compares movements of a first of said one or more individuals to movements of a second of said one or more individuals.

15. The system of claim 1, further comprising:
a respective said sensor attached to each sentinel from said group of sentinels.

16. A system for detecting a health condition of a group of livestock comprising:
a sensor that measures a vitality parameter value for a group of sentinels, said group of sentinels comprising a statistically significant sample of the group of livestock;
a processor that:
assesses a health status of said group of sentinels based on said vitality parameter value;
tracks and records a record of said health status over time; and
detects the health condition of the group of livestock based on said record, and
a data storage unit that stores a datum related to at least one item selected from the group consisting of an output of said sensor, said vitality parameter value, said health status, said record and said health condition;
wherein said processor further analyzes a disorder level based on a percentage of sentinels indicating a decrease in said health status and wherein said record further includes said disorder level, and said processor detects the health condition of the group based also on said disorder level.

17. A system for detecting a health condition of a group of livestock comprising:
a sensor that measures a vitality parameter value for a group of sentinels, said group of sentinels comprising a statistically significant sample of the group of livestock;
a processor that:
assesses a health status of said group of sentinels based on said vitality parameter value;
tracks and records a record of said health status over time; and
detects the health condition of the group of livestock based on said record, and
a data storage unit that stores a datum related to at least one item selected from the group consisting of an output of said sensor, said vitality parameter value, said health status, said record and said health condition;
wherein said processor further identifies one or more individuals from said group of sentinels, and wherein said sensor further measures a respective individual value of said vitality parameter value for each of said one or more individuals;
wherein said processor further monitors a respective individual health status of each of said one or more individuals over time and wherein said record includes said respective individual health status; and
wherein said processor further ranks a plurality of said one or more individuals with respect to at least one item selected from the group consisting of said respective individual value of said vitality parameter value, said respective individual health status and a measured behavior.

18. A system for detecting a health condition of a group of livestock comprising:
a sensor that measures a vitality parameter value for a group of sentinels, said group of sentinels comprising a statistically significant sample of the group of livestock;
a processor that:
assesses a health status of said group of sentinels based on said vitality parameter value;
tracks and records a record of said health status over time; and
detects the health condition of the group of livestock based on said record, and
a data storage unit that stores a datum related to at least one item selected from the group consisting of an output of said sensor, said vitality parameter value, said health status, said record and said health condition;
wherein said processor further identifies one or more individuals from said group of sentinels, and wherein said sensor further measures a respective individual value of said vitality parameter value for each of said one or more individuals; and
wherein said processor further analyzes said respective individual value of said vitality parameter value of each of said one or more individuals to indicate a tendency of a disease to spread in the group of livestock and wherein said health condition is detected based on said tendency.

19. The system according to claim 18, wherein said sensor includes a digital camera and wherein said digital camera covers a specific zone, and said processor identifies an individual from said group of sentinels in said specific zone.

20. The system of claim 18, further comprising:
at least one indicator attached to each of said one or more individuals to facilitate identification of each of said one or more individuals.

* * * * *